United States Patent
Letourneau et al.

(10) Patent No.: US 7,906,504 B2
(45) Date of Patent: *Mar. 15, 2011

(54) 2-(1-OXO-1H-ISOQUINOLIN-2-YL)ACETAMIDE DERIVATIVES

(75) Inventors: Jeffrey Letourneau, East Windsor, NJ (US); Jui-Hsiang Chan, West Windsor, NJ (US); Patrick Jokiel, Princeton, NJ (US); Michael Ohlmeyer, Plainsboro, NJ (US); Irina Neagu, Plainsboro, NJ (US); Christopher Riviello, Morrisville, PA (US); John Richard Morphy, Newhouse (GB); Susan Elizabeth Napier, Newhouse (GB); Koc-Kan Ho, West Windsor, NJ (US)

(73) Assignee: N.V. Organon, Oss (NL)

( * ) Notice: Subject to any disclaimer, the term of this patent is extended or adjusted under 35 U.S.C. 154(b) by 28 days.

This patent is subject to a terminal disclaimer.

(21) Appl. No.: 11/852,737

(22) Filed: Sep. 10, 2007

(65) Prior Publication Data
US 2008/0064678 A1    Mar. 13, 2008

Related U.S. Application Data

(60) Provisional application No. 60/843,713, filed on Sep. 11, 2006.

(51) Int. Cl.
*C07D 217/24* (2006.01)
*A61K 31/472* (2006.01)

(52) U.S. Cl. ............ 514/210.21; 514/309; 546/141

(58) Field of Classification Search ............ None
See application file for complete search history.

(56) References Cited

U.S. PATENT DOCUMENTS
4,438,121 A    3/1984    Obitz

FOREIGN PATENT DOCUMENTS
WO    WO 2006/095014 A1    9/2006

OTHER PUBLICATIONS

West, Anthony R., Solid State Chemistry and its Applications, Wiley, New York, 1988, pp. 358 & 365.*
International Search Report and Written Opinion dated Oct. 3, 2008 for related International Application No. PCT/US07/78022.
International Search Report and Written Opinion dated Oct. 7, 2008 for corresponding International Application No. PCT/US07/77999.
West, Anthony R., "Chapter 10. Solid Solutions", *Solid State Chemistry and Its Applications*, pp. 358 and 365; John Wiley & Sons, Pub., New York (1988).

* cited by examiner

*Primary Examiner* — Zinna N Davis
(74) *Attorney, Agent, or Firm* — Susan L. Hess

(57) ABSTRACT

Disclosed herein are 2-(1-oxo-1H-isoquinolin-2-yl)acetamide derivative of formula I,

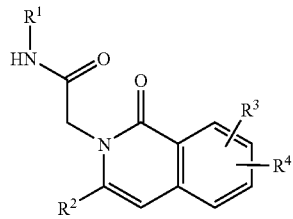

formula I or pharmaceutically acceptable salts or solvates thereof wherein each of the substituents is given the definition as set forth in the specification and claims. Also disclosed are pharmaceutical compositions comprising 2-(1-oxo-1H-isoquinolin-2-yl)acetamide derivatives according to the present invention and their use in therapy.

11 Claims, No Drawings

2-(1-OXO-1H-ISOQUINOLIN-2-YL)ACETAMIDE DERIVATIVES

This application claims benefit of 60/843,713 filed Sep. 11, 2006.

The present invention relates to 2-(1-oxo-1H-isoquinolin-2-yl)acetamide derivatives, to pharmaceutical compositions comprising these compounds and to their use in therapy, in particular to their use for the manufacture of a medicament for the treatment or prevention of disorders or diseases influenced by modulation of the activity of the HPA axis.

The hypothalamo-pituitary-adrenal (HPA) axis is the major stress axis in humans and other mammals. A variety of stressors (and multiple other classes of stimuli) cause release of the hormone ACTH (adrenocorticotropic hormone) from the anterior pituitary gland. ACTH enters the systemic circulation and acts on the adrenal cortex to promote synthesis and release of glucocorticoid hormone (the major endogenous glucocorticoid being cortisol in humans and corticosterone in rodents). The glucocorticoids exert a broad spectrum of effects, the main purpose of which is to mobilise energy sources for successful responsiveness and eventual adaptation to the stressor.

Abnormally elevated HPA axis activity in man is associated with the development of a variety of psychiatric disturbances, some of which are stress-related in aetiology. Elevated cortisol levels, which are indicative of HPA axis hyperactivity and loss of normal negative feedback regulatory processes, are a common finding in affective disorders and various other psychiatric disturbances, and are widely utilised as a diagnostic tool (Holsboer et al., *Biol. Psych.*, 1986, 21, 601-611). It is generally considered that dysregulation of the HPA axis is a relection of enhanced vulnerability and poor adaptation to chronic stress and that chronic stress therefore plays a major role in the development of affective illness (Sperry and Carlson, DSM-IV diagnosis to treatment, 2$^{nd}$ Edition, Taylor & Francis, 1996). This central concept is supported by experimental evidence utilising animal models of chronic stress, where abherent HPA function closely resembles that seen in clinical settings (De Goeij et al., *Neuroendocrinology*, 1991, 53, 150-159; Plotsky and Meaney, *Mol. Brain Res.*, 1993, 18, 195-200).

The major secretagogues for ACTH in humans and rats are CRH (corticotropin releasing hormone) and AVP (arginine vasopressin). Within the HPA axis these peptide hormones are synthesised by the parvocellular neurones of the paraventricular nucleus (PVN) of the hypothalamus. The axons of these neurones project to the external zone of the median eminence, from where the hormone products enter the hypophysial portal system to bathe the corticotrope cells that manufacture ACTH. CRH and AVP act synergistically at the corticotrope to regulate ACTH secretion in both rats (Rivier and Vale, *Nature*, 1983, 305, 325-327) and in man (De Bold et al., *J. Clin. Invest.*, 1984, 73, 533-538).

The actions of AVP at the pituitary cortocotrope are mediated by the vasopressin $V_3$ (or $V_{1b}$) receptor, which is known and has been cloned (human receptor: Sugimoto et al., *J. Biol. Chem.*, 1994, 269, 27088-27092). A report of clinical studies in depressed patients in which blunted ACTH responses to CRH could be restored by concomitant administration of desmopressin (dDAVP, an AVP agonist with $V_3$ affinity) confirms the involvement of the $V_3$ receptor in depression (Scott and Dinan, *Life Sciences*, 1998, 62, 1985-1988). A study in rodents with non-selective peptide $V_3$ antagonists indicates that the $V_3$ receptor does play a functional role in control of pituitary ACTH release (Bernardini et al., *Neuroendocrinology*, 1994, 60, 503-508). Vasopressin antagonists are thus utilised to modulate and normalise pituitary ACTH release and subsequent HPA axis dysfunction in CNS disorders which are characterised by abnormal HPA axis negative feedback mechanisms.

In addition to the $V_3$ receptor, vasopressin also activates peripheral receptors, i.e., the $V_{1a}$ receptor, predominantly found on liver and vascular tissue and the $V_2$ receptor, predominantly found on kidney tissue. Interaction at these receptors mediate the pressor and antidiuretic actions of AVP.

Whilst there are several non-peptide low-molecular weight antagonists known which are selective for the $V_{1a}$ or the $V_2$ receptor (for a recent review see Freidinger and Pettibone, *Medicinal Research Reviews*, 1997, 17, 1-16), there are only a small number of non-peptide ligands known with selectivity for the $V_3$ receptor (see for example, WO 01/55130 and WO 04/009585). There exists therefore a need for further non-peptide $V_3$ selective antagonists which are both safe and effective.

In a first aspect, the present invention provides a 2-(1-oxo-1H-isoquinolin-2-yl)acetamide derivative of formula I

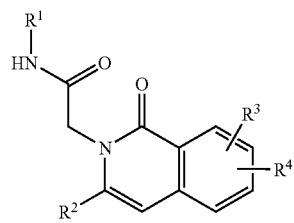

formula I wherein
$R^1$ is $C_{1-6}$alkyl, $C_{3-6}$cycloalkyl, $C_{3-6}$cycloalkyl$C_{1-12}$alkyl, $C_{2-6}$alkenyl or $C_{2-6}$alkynyl, said $C_{1-6}$alkyl, $C_{3-6}$cycloalkyl and $C_{3-6}$cycloalkyl$C_{1-2}$alkyl being optionally substituted with one or more halogens;
$R^2$ is $C_{6-10}$aryl optionally substituted with one to three substituents selected from halogen, hydroxy, cyano, $C_{1-6}$alkyl, $C_{3-6}$cycloalkyl, $C_{1-6}$alkyloxy and $C_{3-6}$cycloalkyloxy, said $C_{1-6}$alkyl, $C_{3-6}$ cycloalkyl, $C_{1-6}$ alkyloxy and $C_{3-6}$cycloalkyloxy being optionally substituted with one or more halogens or $R^2$ is a 5-10 membered heteroaryl ring system comprising a heteroatom selected from N, O, S and optionally substituted with a substituent selected from methyl, $C_{1-6}$alkyloxy and halogen;
$R^3$ is an optional substituent selected from $C_{1-6}$alkyl, $C_{1-6}$alkyloxy and halogen, said $C_{1-6}$alkyl and $C_{1-6}$alkyloxy being optionally substituted with one or more halogens;
$R^4$ is a group located at the 6- or 7-position of the oxoisoquinoline ring and is selected from

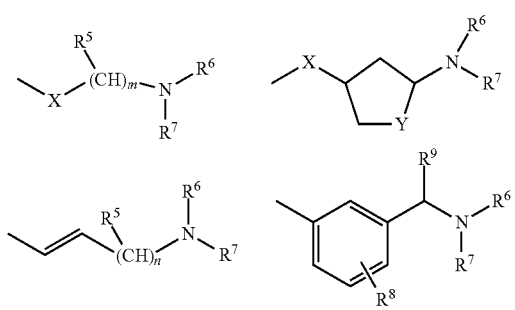

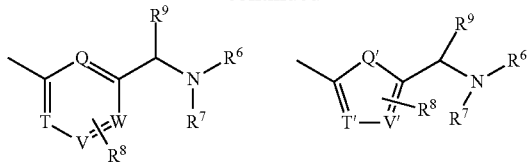

each $R^5$ is independently H or $C_{1-6}$alkyl or one of $R^5$ when joined together with one of $R^6$ or $R^7$ forms a 4-7 membered heterocyclic ring;

$R^6$ and $R^7$ are independently H, $C_{1-6}$alkyl, $C_{3-6}$cycloalkyl, $C_{3-6}$cycloalkyl$C_{1-2}$alkyl, $C_{6-10}$ aryl or $C_{6-10}$aryl$C_{1-2}$alkyl; or $R^6$ and $R^7$ together with the nitrogen to which they are bonded form a 4 to 8 membered saturated or unsaturated heterocyclic ring optionally comprising a further heteroatomic moiety selected from O, S and $NR^{10}$, said heterocyclic ring being optionally substituted with one or two substituents selected from halogen, hydroxyl, $C_{1-6}$alkyl, $C_{1-6}$alkyloxy, cyano and $COOR^{11}$ and said heterocyclic ring being optionally fused at two adjacent carbon atoms to a phenyl ring;
or one of $R^6$ and $R^7$ when joined together with one of $R^5$ forms a 4-7 membered heterocyclic ring;
or one of $R^6$ and $R^7$ when joined together with one of $R^8$ forms a 5-6 membered heterocyclic ring;

$R^8$ is one or two substituents selected from H, $C_{1-6}$alkyl, $C_{1-6}$alkyloxy and halogen or one of $R^8$ when joined together with one of $R^6$ and $R^7$ forms a 5-6 membered heterocyclic ring;
or one of $R^8$ when joined together with $R^9$ forms a 5-6 membered ring $R^9$ is H or $C_{1-6}$alkyl or $R^9$ when joined together with one of $R^8$ forms a 5-6 membered ring;

$R^{10}$ is H, $C_{1-6}$alkyl or $C_{1-6}$acyl;

$R^{11}$ is H or $C_{1-6}$alkyl;

m is 2-4;

n is 1-3;

X is $CH_2$, O, S, $SO_2$ or $NR^{12}$;

$R^{12}$ is H, $C_{1-6}$alkyl, $C_{1-6}$acyl or $C_{6-10}$aryl$C_{1-2}$alkyl group, said $C_{6-10}$aryl$C_{1-2}$alkyl group being optionally substituted with methyl or methoxy;

Y is $CH_2$, $(CH_2)_2$ or $(CH_2)_3$;

Q, T, V and W are C or N with the proviso that one of Q, T, V and W is N and the others are C;

Q', T' and V' are selected from C, O, N and S with the proviso that one of Q', T' and V' is O, N, or S and the others are C;
or a pharmaceutically acceptable salt or solvate thereof.

The term $C_{1-6}$ alkyl, as used herein, represents a branched or unbranched alkyl group having 1-6 carbon atoms. Examples of such groups are methyl, ethyl, isopropyl, tertiary-butyl, pentyl and hexyl.

The term $C_{2-6}$ alkenyl, as used herein, represents a branched or unbranched alkenyl group having 2-6 carbon atoms and at least one double bond. Examples of such groups are ethenyl and 3-methylbutynyl.

The term $C_{2-6}$ alkynyl, as used herein, represents a branched or unbranched alkynyl group having 2-6 carbon atoms and at least one triple bond. Examples of such groups are ethynyl and 3-methylbutynyl.

The term $C_{3-6}$ cycloalkyl, as used herein, represents a branched or unbranched cyclic alkyl group having 3-6 carbon atoms. Examples of such groups are cyclopropyl, cyclopentyl and 2-methylcyclopentyl.

The term $C_{3-6}$cycloalkyl$C_{1-2}$alkyl, as used herein, represents a $C_{1-2}$ alkyl group which is substituted with a $C_{3-6}$cycloalkyl group. Examples of such groups are cyclopropylmethyl and 2-cyclobutylethyl.

The term $C_{1-6}$ alkyloxy, as used herein, represents a branched or unbranched alkyloxy group having 1-6 carbon atoms. Examples of such groups are methoxy, ethoxy, isopropyloxy and tertiary-butyloxy.

The term $C_{3-6}$ cycloalkyloxy, as used herein, represents a branched or unbranched cyclic alkyloxy group having 3-6 carbon atoms. Examples of such groups are cyclopropyloxy, cyclopentyloxy and 2-methylcyclopentyloxy. Similarly, the term $C_{4-6}$ cycloalkyloxy represents a branched or unbranched cyclic alkyloxy group having 4-6 carbon atoms.

The term $C_{1-6}$ acyl, as used herein, represents an acyl group derived from a carboxylic acid having 1-6 carbon atoms. The acyl group can comprise a hydrocarbon which may be branched, unbranched, saturated or unsaturated. Examples of such groups include formyl, acetyl, propionyl, acryloyl and pivaloyl. Also included within the definition of $C_{1-6}$ acyl are groups derived from dicarboxylic acids like groups derived from malonic acid.

The term $C_{6-10}$ aryl, as used herein, represents an aromatic group having 6-10 carbon atoms. Examples of such groups include phenyl and naphthyl.

The term $C_{6-10}$aryl$C_{1-2}$alkyl, as used herein, represents a $C_{1-2}$ alkyl group which is substituted with a $C_{6-10}$ aryl group. Examples of such groups include benzyl and phenethyl.

The term halogen, as used herein, represents a fluorine, chlorine, bromine or iodine.

The term 5-10 membered heteroaryl ring system comprising a heteroatom selected from N, O and S, as used herein, represents a monocyclic or fused bicyclic 5-10 membered heteroaryl ring system comprising a heteroatom selected from N, O and S. Examples of such groups include furanyl, thienyl, pyrrolyl, pyridinyl, indolyl, benzothienyl and quinolinyl.

Examples of 4 to 8 membered saturated or unsaturated heterocyclic rings formed by $R^6$ and $R^7$ together with the nitrogen to which they are bonded and optionally comprising a further heteroatomic moiety selected from O, S and $NR^{10}$ wherein $R^6$, $R^7$ and $R^{10}$ have the previously defined meanings, as used herein, include piperidine, homopiperidine, morpholine, thiomorpholine, 4-methylpiperazine, tetrahydropyridine and 4-methylhomopiperazine.

In one embodiment of the present invention $R^1$ is $C_{1-6}$alkyl, $C_{3-6}$cycloalkyl or $C_{3-6}$ cycloalkyl$C_{1-2}$alkyl. In a further embodiment $R^1$ is $C_{3-4}$alkyl, $C_{3-4}$cycloalkyl or $C_{3-4}$ cycloalkyl$C_{1-2}$alkyl. In a further embodiment $R^1$ is isopropyl, isobutyl, tertiary-butyl or cyclopropylmethyl.

In another embodiment $R^2$ is $C_{6-10}$aryl, optionally substituted with one to three substituents selected from halogen, hydroxy, cyano, $C_{1-6}$alkyl, $C_{3-6}$cycloalkyl, $C_{1-6}$alkyloxy and $C_{3-6}$ cycloalkyloxy, said $C_{1-6}$alkyl, $C_{3-6}$ cycloalkyl, $C_{1-6}$ alkyloxy and $C_{3-6}$cycloalkyloxy being optionally substituted with one or more halogens. In a further embodiment $R^2$ is a phenyl ring. In a further embodiment $R^2$ is a 3-substituted phenyl ring. In a further embodiment $R^2$ is a 3-substituted phenyl ring substituted with one to three substituents selected from chloro, fluoro, $C_{1-2}$alkyl, trifluoromethyl, $C_{1-3}$alkyloxy, $C_{1-4}$ cycloalkyloxy and trifluoromethoxy. In a further embodiment $R^2$ is a substituted phenyl ring selected from 3-chlorophenyl, 3-fluorophenyl, 3-methoxyphenyl, 3-trifluoromethoxyphenyl, 3-chloro-4-fluorophenyl and 4-fluoro-3-methoxyphenyl.

In another embodiment $R^2$ is a 5-10 membered heteroaryl ring system comprising a heteroatom selected from N, O and S and optionally substituted with a substituent selected from methyl, $C_{1-6}$alkyloxy and halogen. In a further embodiment $R^2$ is a 2-thienyl, 3-thienyl, 2-pyridyl or 6-indolyl optionally substituted with chloro, methyl or methoxy.

In another embodiment, $R^4$ is the group

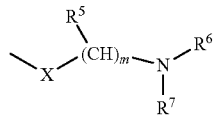

wherein X, m and $R^5$-$R^7$ have the meanings as defined previously. In a further embodiment $R^5$ is H or methyl and m is 3. In a further embodiment $R^4$ is a group selected from

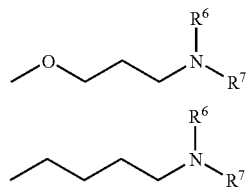

wherein $R^6$ and $R^7$ have the meanings as defined previously.

In another embodiment, $R^4$ is the group

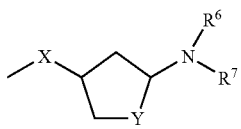

wherein X, Y, $R^6$ and $R^7$ have the meanings as defined previously. In a further embodiment X is O or $CH_2$ and Y is $CH_2$.

In another embodiment, $R^4$ is the group

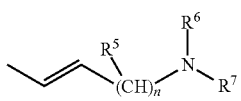

wherein n and $R^5$-$R^7$ have the meanings as defined previously. In a further embodiment $R^5$ is methyl and n is 2.

In another embodiment $R^4$ is the group

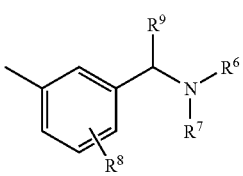

wherein $R^6$ to $R^9$ have the meanings as defined previously. In a further embodiment $R^8$ and $R^9$ are H.

In another embodiment, $R^4$ is the group

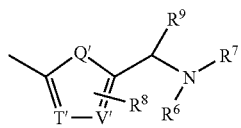

wherein Q', T', V' and $R^6$-$R^9$ have the meanings as defined previously. In a further embodiment $R^8$ and $R^9$ are both H.

In another embodiment, $R^4$ is the group

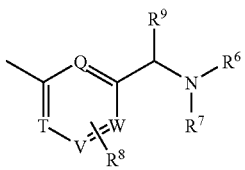

wherein Q, T, V, W and $R^6$-$R^9$ have the meanings as defined previously. In a further embodiment $R^8$ and $R^9$ are both H.

In another embodiment, $R^4$ is a group selected from

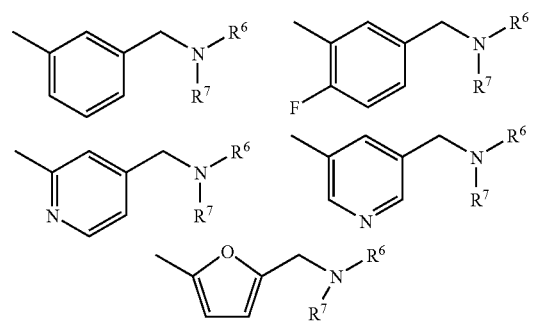

wherein $R^6$ and $R^7$ have the meanings as defined previously.

In another embodiment $R^6$ and $R^7$ are independently H. $C_{1-6}$alkyl, $C_{3-6}$cycloalkyl, $C_{3-6}$cycloalkyl$C_{1-2}$alkyl, $C_{6-10}$aryl or $C_{6-10}$aryl$C_{1-2}$alkyl. In a further embodiment $R^6$ and $R^7$ are independently H or $C_{1-4}$alkyl.

In another embodiment, $R^6$ and $R^7$ together with the nitrogen to which they are bound form a 4 to 7 membered heterocyclic ring optionally comprising a further heteroatomic moiety selected from O, S or $NR^{10}$, said heterocyclic ring being optionally substituted with a hydroxyl substituent wherein $R^{10}$ has the previously defined meaning. In a further embodiment $R^6$ and $R^7$ together with the nitrogen to which they are bound form a heterocyclic ring selected from pyrrolidine, piperidine, 3-hydroxypiperidine and morpholine.

In a further embodiment is a 2-(1-oxo-1H-isoquinolin-2-yl)acetamide selected from:
N-tert-Butyl-2-[3-(4-fluoro-3-methoxyphenyl)-1-oxo-7-(3-pyrrolidin-1-ylpropoxy)-1H-isoquinolin-2-yl]acetamide;
2-[3-(3-Chlorophenyl)-7-((S)-2-methyl-3-pyrrolidin-1-ylpropoxy)-1-oxo-1H-isoquinolin-2-yl]-N-isopropylacetamide and
N-tert-Butyl-2-[3-(3-chloro-4-fluorophenyl)-1-oxo-7-(3-pyrrolidin-1-ylpropoxy)-1H-isoquinolin-2-yl]acetamide
or a pharmaceutically acceptable salt or solvate thereof.

The compounds of the present invention are prepared by methods well known in the art of organic chemistry. See, for example, J. March, '*Advanced Organic Chemistry*' $4^{th}$ Edition, John Wiley and Sons. During synthetic sequences it may be necessary and/or desirable to protect sensitive or reactive groups on any of the molecules concerned. This is achieved by means of conventional protecting groups, such as those described in T. W. Greene and P. G. M. Wuts 'Protective Groups in Organic Synthesis' 2nd Edition, John Wiley and Sons, 1991. The protective groups are optionally removed at a convenient subsequent stage using methods well known in the art.

Compounds of formula I wherein $R^4$ is the group

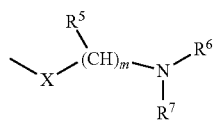

and X is O (shown as 10 below) can be prepared by the general five stage synthetic sequence shown in Scheme 1. Firstly a suitably functionalised 2-halobenzoic acid ester of formula 2, is reacted with a suitably functionalised styrene of formula 3 in the presence of a suitable Pd(II) catalyst (for example palladium diacetate), a triarylphosphine ligand (for example tri(o-tolyl)phosphine) and a tertiary amine base (for example triethylamine) in a polar aprotic solvent (for example acetonitrile) to give the coupled product 4. P represents a suitable protecting group, for example methyl. The 2-halobenzoic acids 2 and styrenes 3 are either commercially available or they can readily be prepared by procedures well known in the art. The carboxylic acid ester 4 is then hydrolysed to the carboxylic acid 5 using either acid or base in a suitable solvent such as ethanol. The carboxylic acid intermediate 5 is subsequently cyclised to the isocoumarin 6 using a palladium(II) catalyst, for example, bis(acetonitrile)dichloropalladium(II) and an oxidant, for example, p-benzoquinone, in an inert solvent, for example, tetrahydrofuran. The isocoumarin 6 thus obtained is heated together with a glycine amide 7 to provide the isoquinolinone 8 which is subsequently deprotected. The free hydroxyl group is then functionalised with an alcohol of formula 9 utilizing, for example, standard Mitsunobu reaction conditions, i.e., in the presence of triphenylphosphine and diethylazodicarboxylate or DIAC to provide the desired product 10. Alcohols of formula 9 are either commercially available or they can readily be prepared by procedures well known in the art.

Scheme 1

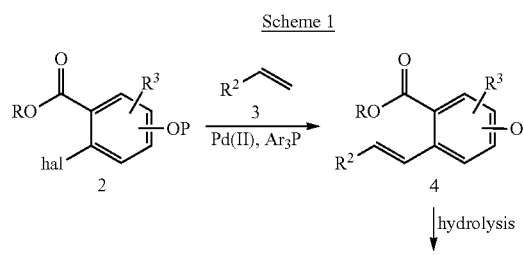

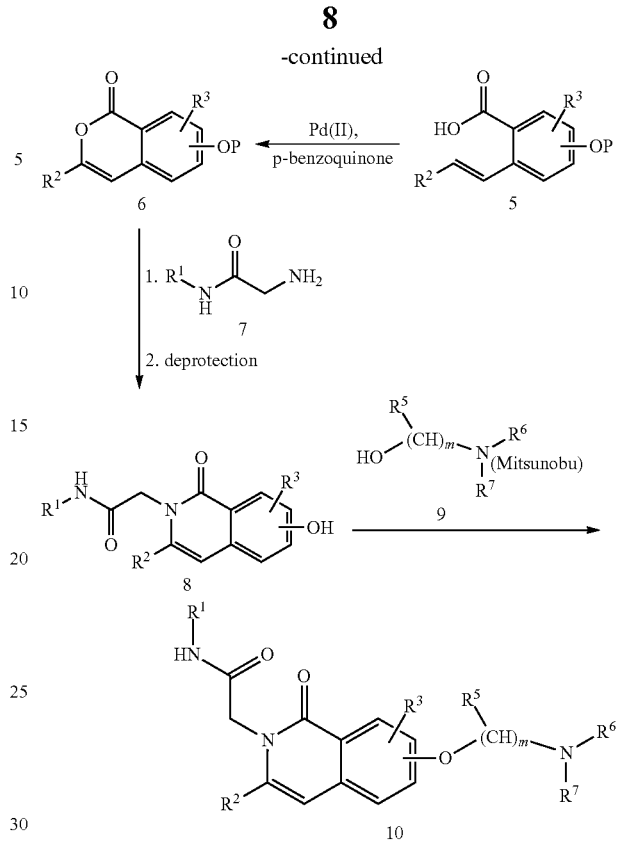

The desired products 10 can also be prepared by alkylation of the hydroxy isoquinolinone 8 in the presence of a suitable base with a compound of formula 11 wherein L is a suitable leaving group. A suitable base would be, for example, a metal carbonate such as potassium carbonate or cesium carbonate. Suitable leaving groups would be, for example, a mesylate or tosylate group or a halide (Scheme 2). Compounds of formula 11 are either commercially available or they can readily be prepared by procedures well known in the art.

Scheme 2

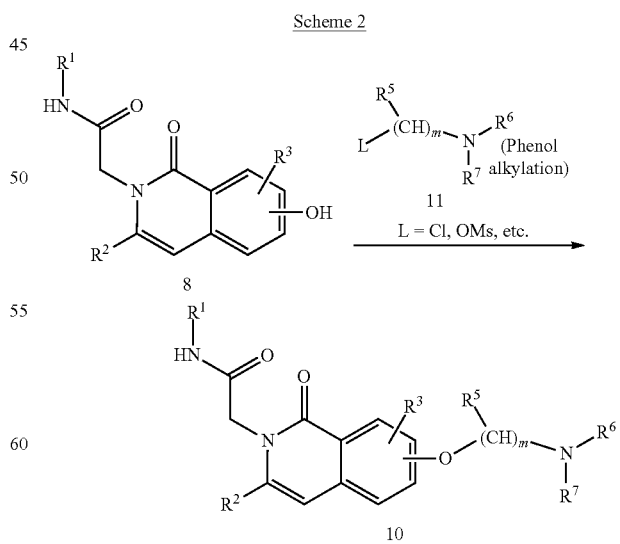

The desired products 10 can also alternatively be prepared by a two-step procedure involving first, a base-mediated alkylation of a hydroxy isoquinolinone 8, with a suitable dihaloalkane, such as 3-bromo-1-chloropropane, followed by nucleophilic displacement with an amine of formula $HNR^6R^7$ (Scheme 3). Dihaloalkanes and amines of formula $HNR^6R^7$ are either commercially available or they can readily be prepared by procedures well known in the art.

Scheme 3

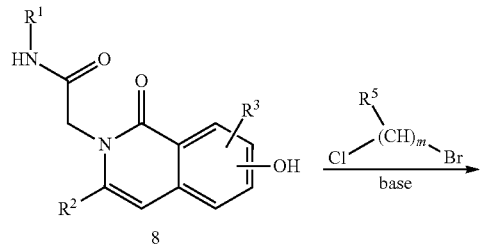

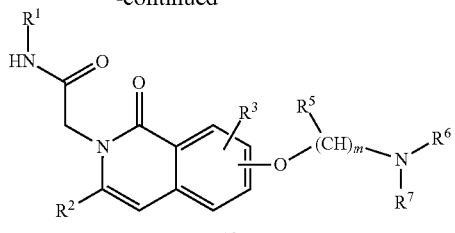

A related three-step procedure by which the desired products 10 can also be prepared involves firstly alkylation of the aforementioned hydroxy isoquinolinone 8 with a suitable haloalkanol, such as 3-bromopropan-1-ol, followed by conversion of the hydroxyl group to a suitable leaving group, such as halide or mesylate, utilizing various methods known to one skilled in the art, and finally, displacement of said leaving group with an amine of formula $HNR^6R^7$ to provide the desired product 10 (Scheme 4). The 2-haloalkanols are either commercially available or they can readily be prepared by procedures well known in the art.

Scheme 4

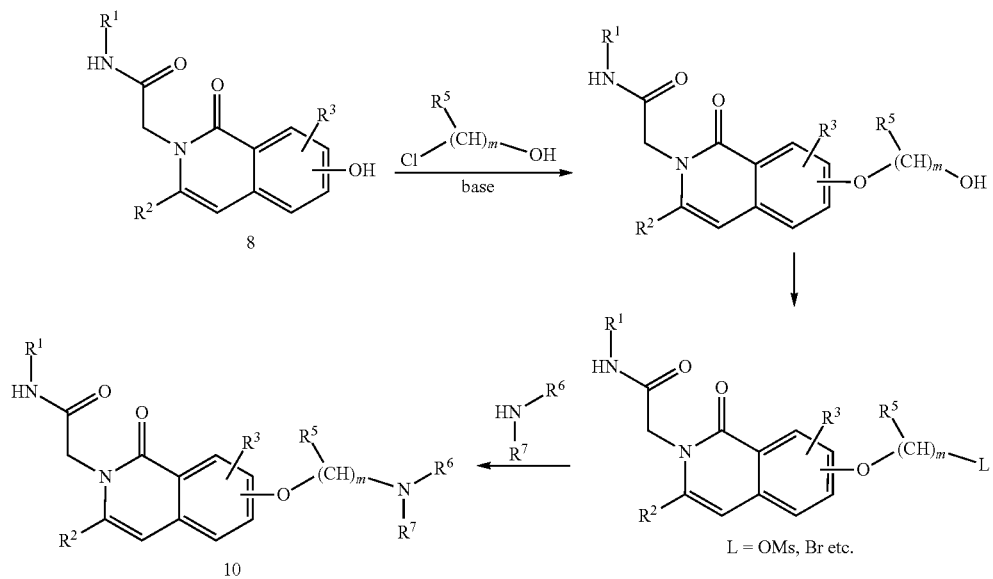

-continued

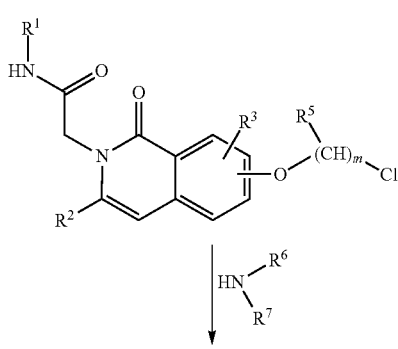

Compounds of formula I wherein $R^4$ is a group having the formula

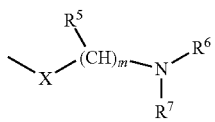

and X is $NR^{12}$ (13) can be prepared by reaction of intermediates of formula I wherein $R^4$ is a suitably reactive group such as a triflate, with diamines of formula 12 in the presence of a suitable catalyst system, such as $Pd_2(dba)_3$ and BINAP, under conditions well known in the art (Scheme 5). Intermediates of formula I wherein $R^4$ is triflate can readily be prepared from the corresponding alcohols 8 using procedures well known in the art, for example by treatment of alcohols 8 with trifluoromethanesulfonic anhydride and pyridine. Diamines of formula 12 are either commercially available or they can readily be prepared by procedures well known in the art.

and X is O or $NR^{12}$ can be prepared using analogous procedures and/or reaction sequences to those described above in Schemes 1-5.

Compounds of formula I, wherein $R^4$ is the group

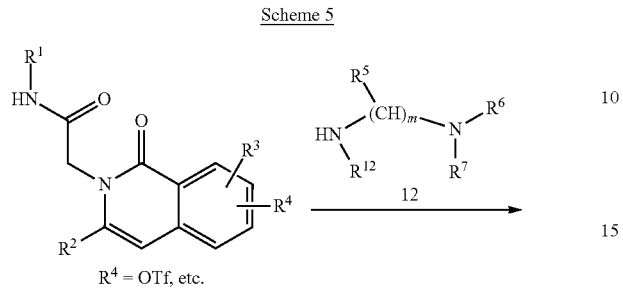

Scheme 5

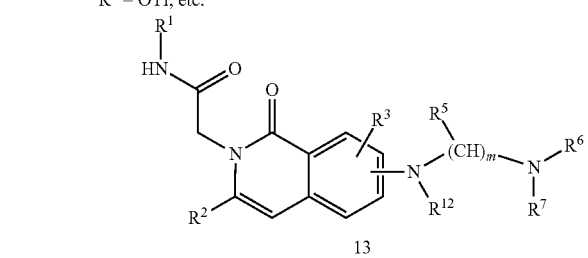

Compounds of formula I wherein $R^4$ is

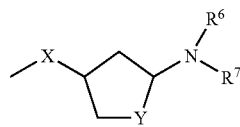

(16) can be prepared by first reacting an intermediate of formula I wherein $R^4$ is a group such as triflate with a terminal alkene of formula 14 (wherein L is a displaceable group such as halide or a group such as hydroxyl which can subsequently be converted to a displaceable group such as halide, mesylate, or tosylate) in the presence of a base such as triethylamine, a suitable catalyst such as $Pd(OAc)_2$, and a triarylphosphine ligand such as tri(o-tolyl)phosphine to give the intermediate 15. The amine 16 is then formed from the alkene 15 by displacement of leaving group L with an aliphatic amine of formula $HNR^6R^7$. The corresponding saturated derivative 17 can be obtained by hydrogenation of the unsaturated amine 16 in the presence of, for example, a palladium on carbon catalyst (Scheme 6). Alkenes of formula 14 are either commercially available or they can readily be prepared by procedures well known in the art.

Scheme 6

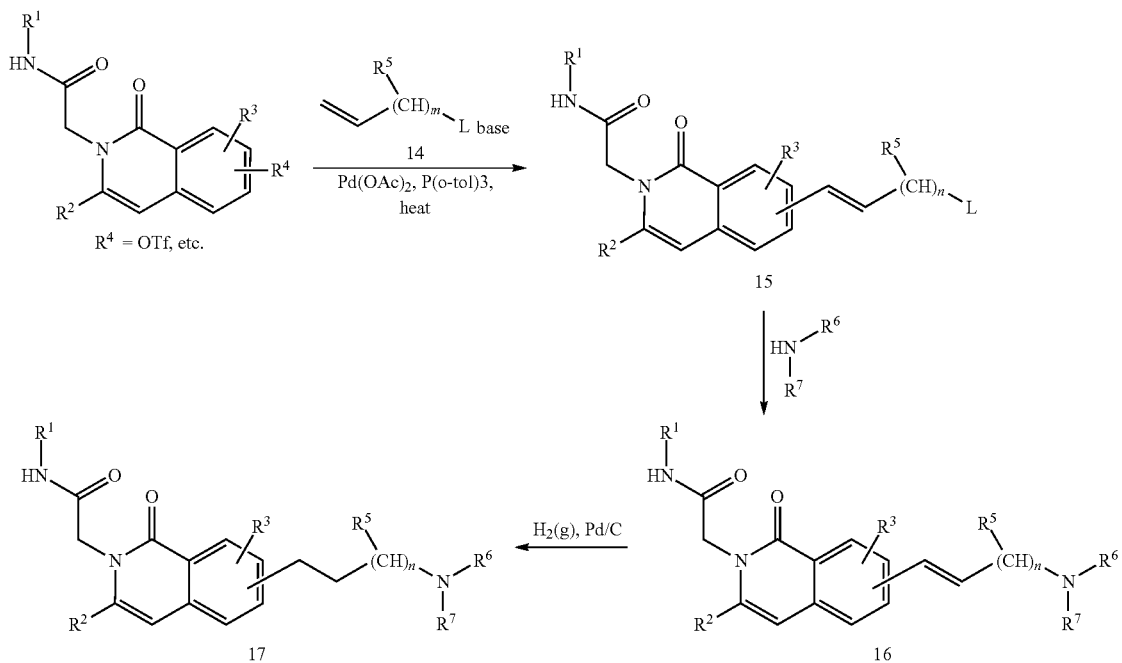

Compounds of formula I, wherein $R^4$ is the group

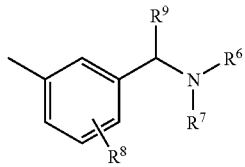

(23) can be prepared by coupling of an intermediate of formula I wherein $R^4$ is a suitably reactive group such as triflate, with a boronic acid or ester of formula 18 or 19 (A=B(OH)$_2$ or B(OR)$_2$)

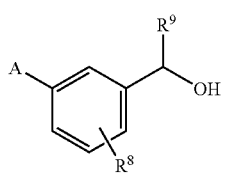

18

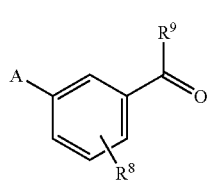

19 in the presence of a suitable catalyst such as Pd(PPh$_3$)$_4$ followed by conversion to the desired amine by a variety of methods familiar to one skilled in the art. For example, adduct 21 can be obtained upon reaction of intermediate of formula I, wherein $R^4$ is triflate with the boronate 20 in the presence of Pd(PPh$_3$)$_4$. This can then be converted to intermediate 22 in which the hydroxyl group has been converted to a leaving group, such as halide or mesylate. Compound 22 can then in turn be treated with an amine of formula HNR$^6$R$^7$ to afford the desired product 23 (Scheme 7). Compounds of formula 18, 19, 20 are either commercially available or they can readily be prepared by procedures well known in the art.

Scheme 7

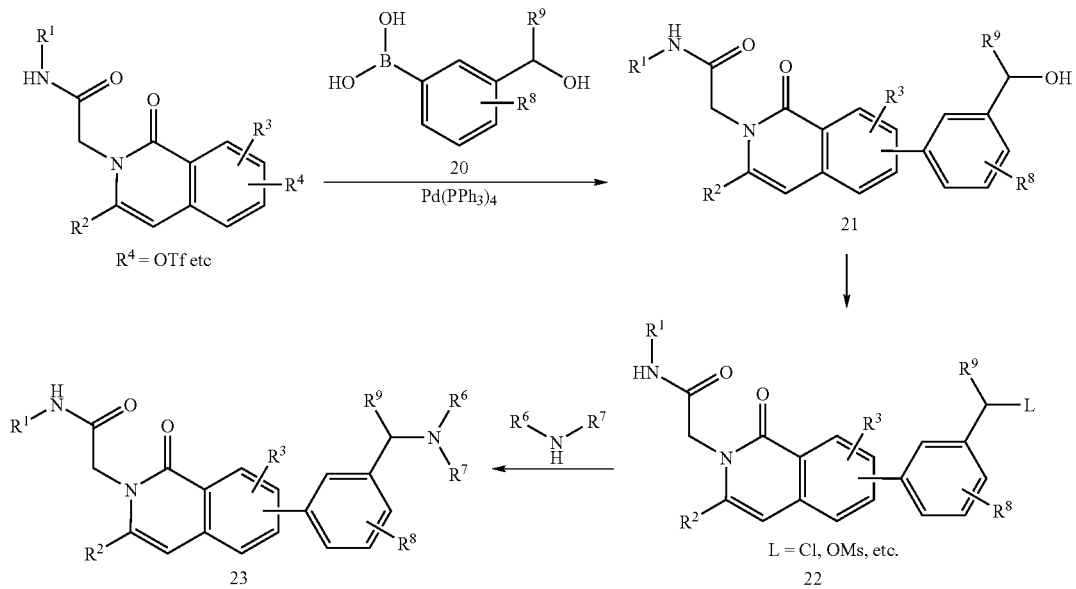

Alternatively, adduct 25 can be obtained by reaction of intermediate of formula I with boronate 24. This can then be converted to the desired amine product 23 upon treatment with HNR$^6$R$^7$ in the presence of a suitable reducing agent such as sodium triacetoxyborohydride or sodium cyanoborohydride (Scheme 8). Boronates 24 are either commercially available or they can readily be prepared by procedures well known in the art.

Scheme 8

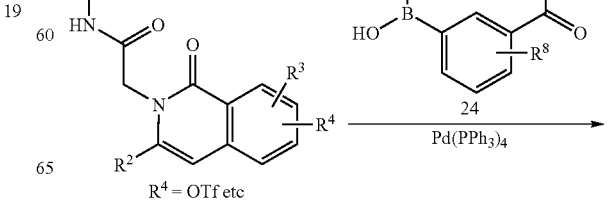

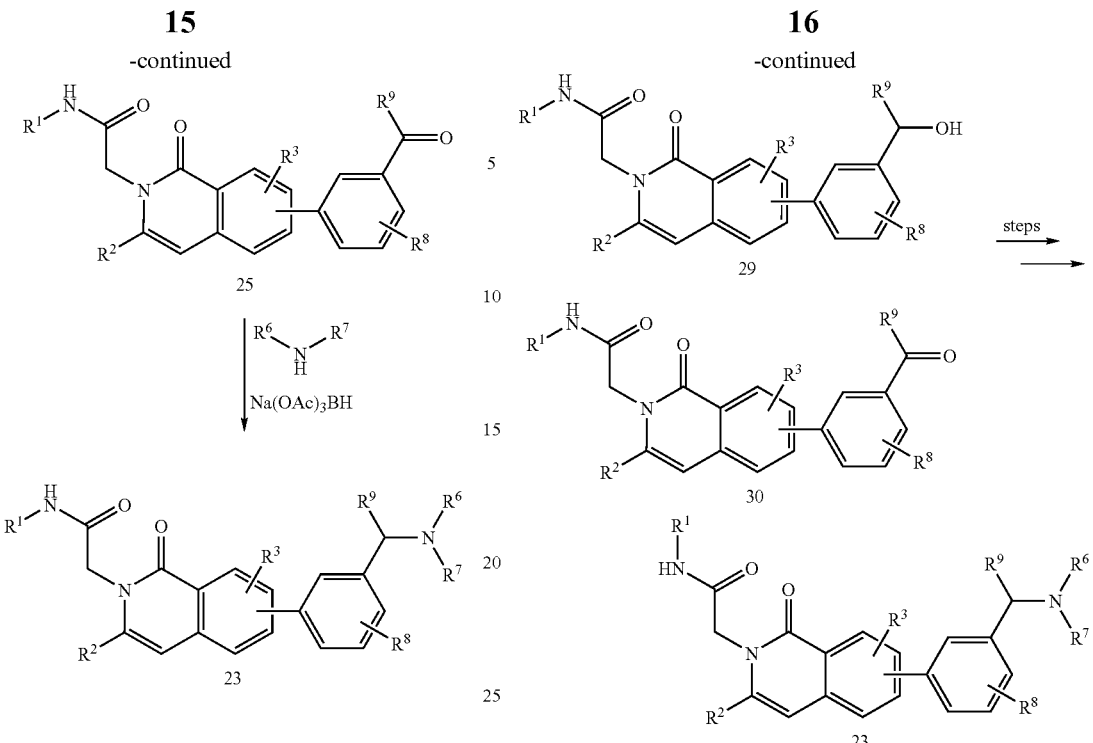

A further method by which the desired products (23) can be obtained involves coupling of an intermediate boronate (26), prepared via an intermediate halide or triflate of formula I ($R^4$=halide or triflate) by reaction of said halide or triflate with bis(pinacolato)diboron in the presence of a suitable catalyst such as $PdCl_2$(dppf) and a base such as KOAc (Scheme 9). This can then be coupled with an aryl halide or triflate of formula 27 or 28 (A=halide or triflate) using analogous procedures to those shown in Schemes 7 and 8 to provide the adducts 29 and 30 which are then converted to the product 23.

Scheme 9

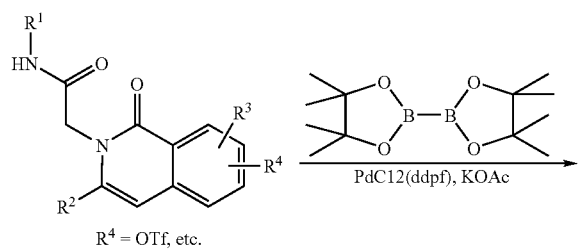

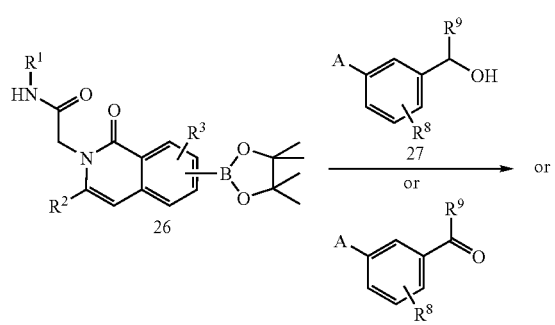

Compounds of formula I, wherein $R^4$ is a group selected from

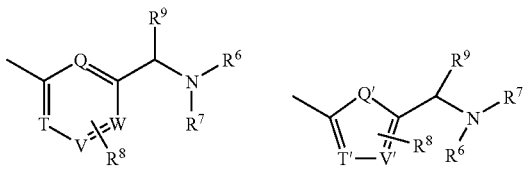

can prepared using the same general procedures and/or reaction sequences described above in Schemes 7-9.

It will be readily appreciated by one skilled in the art that the isoquinolinones of general formula I can be prepared using the general procedures and/or reaction sequences described above in any suitable order. For example, whereas the processes detailed above describe introduction of the $R^4$ groups later in the syntheses utilizing preformed isoquinolinone intermediates, it will be recognized that, in some cases, the $R^4$ groups can be introduced before the formation of the isoquinolinone ring system.

Hence compounds of formula I wherein $R^4$ is a group having the formula

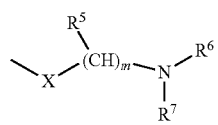

and X is O can be prepared in 5 stages from phenol 31 as shown in Scheme 10. The phenol 31 is either commercially available or prepared using procedures well known in the art of organic chemistry. The phenol can be alkylated using analogous procedures to those shown above in Schemes 1-4 to provide the amino ether 32. This is then coupled with the styrene 3 in an analogous manner to that indicated in Scheme 1 to provide the coupled product 33. Upon treatment with either aqueous acid or base in a suitable solvent, for example, using hydrochloric acid in ethanol, the ester group can then be hydrolysed to yield the benzoic acid intermediate 34. This is subsequently cyclised to the isocoumarin 35 using a palladium(II) catalyst, for example, bis(acetonitrile)dichloropalladium(II) and an oxidant, for example, p-benzoquinone, in an inert solvent, for example, tetrahydrofuran. The isocoumarin 35 is subsequently reacted with the glycine amide 7, using analogous procedures to those indicated previously (see Scheme 1) to yield the isoquinolinone 10.

The present invention also includes within its scope all stereoisomeric forms of 2-(1-oxo-1H-isoquinolin-2-yl)acetamide derivatives resulting, for example, because of configurational or geometrical isomerism. Such stereoisomeric forms are enantiomers, diastereoisomers, cis and trans isomers etc. For example, in the case where $R^1$ is 2-methylbutyl the compound exists as a pair of enantiomers. In the case where $R^4$ comprises an alkene fragment, both (Z) and (E) stereoisomeric forms of the compound are possible. In the case of the individual enantiomers of compounds of formula I or salts or solvates thereof, the present invention includes the aforementioned stereoisomers substantially free, i.e., associ-

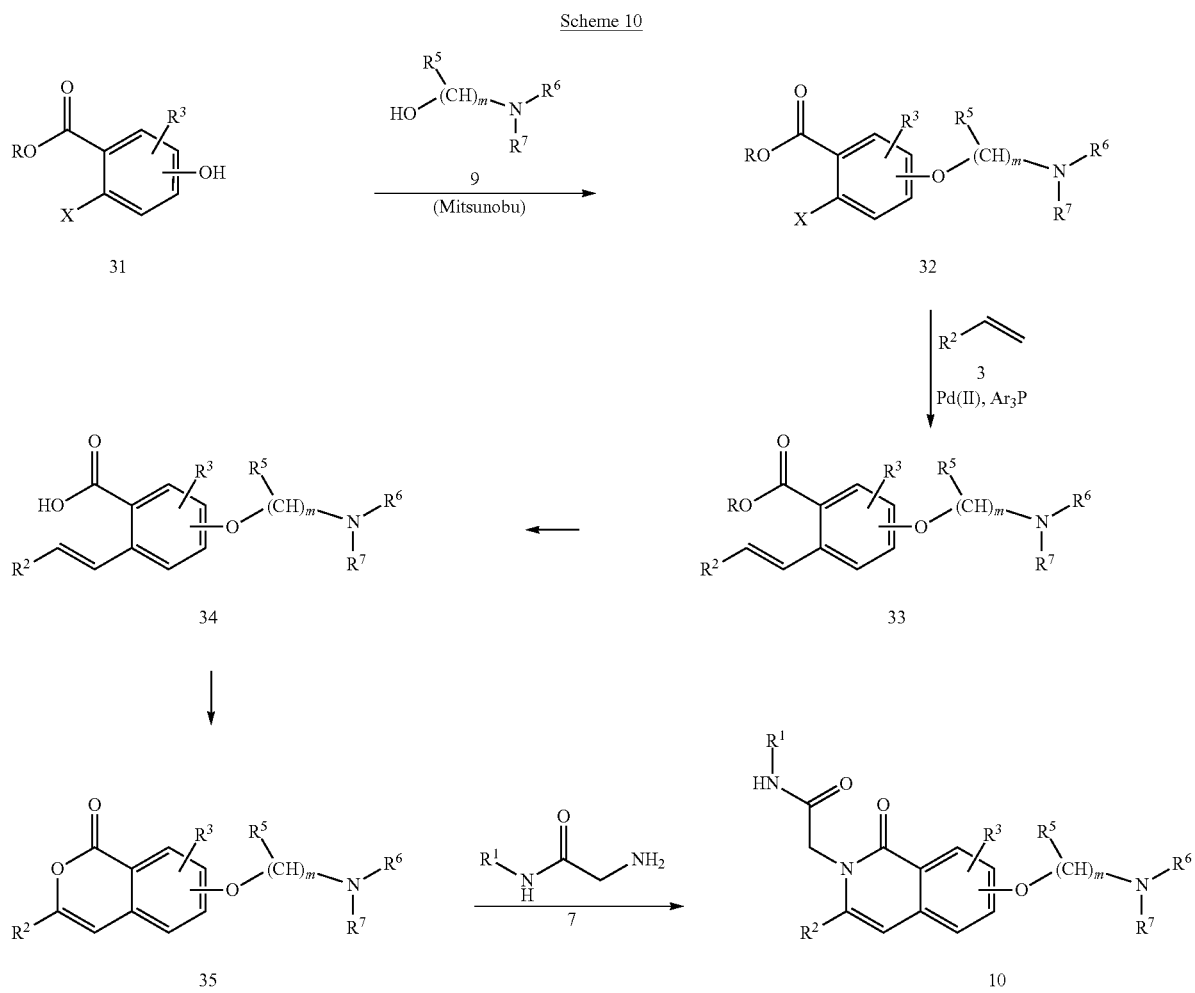

Compounds of formula I wherein $R^4$ is a group having the formula

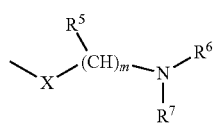

and X is $SO_2$ can be prepared by oxidation of the corresponding sulphides using, for example, m-chloroperoxybenzoic acid in dichloromethane.

ated with less than 5%, preferably less than 2% and in particular less than 1% of the other enantiomer. Mixtures of stereoisomers in any proportion, for example a racemic mixture comprising substantially equal amounts of two enantiomers are also included within the scope of the present invention.

For chiral compounds, methods for asymmetric synthesis whereby the pure stereoisomers are obtained are well known in the art, e.g., synthesis with chiral induction, synthesis starting from chiral intermediates, enantioselective enzymatic conversions, separation of stereoisomers using chromatography on chiral media. Such methods are described in *Chirality In Industry* (edited by A. N. Collins, G. N. Sheldrake and J. Crosby, 1992; John Wiley). Likewise methods for synthesis of geometrical isomers are also well known in the art.

The present invention also includes within its scope all isotopically labelled forms of the 2-(1-oxo-1H-isoquinolin-2-yl)acetamide derivatives of the invention. For example, compounds isotopically labelled with $^2$H, $^3$H, $^{11}$C, $^{13}$C, $^{14}$C, $^{131}$I, $^{125}$I, $^{123}$I and $^{18}$F. The labelled compounds are useful as diagnostic tools, radio tracers, or monitoring agents in various diagnostic methods and for in vivo receptor imaging.

The 2-(1-oxo-1H-isoquinolin-2-yl)acetamide derivatives of the present invention, in the form as a free base, are isolated from reaction mixtures as pharmaceutically acceptable salts. These salts are also obtained by treatment of said free base with an organic or inorganic acid, for example, hydrogen chloride, hydrogen bromide, hydrogen iodide, sulfuric acid, phosphoric acid, acetic acid, trifluoroacetic acid, propionic acid, glycolic acid, maleic acid, malonic acid, methanesulfonic acid, fumaric acid, succinic acid, tartaric acid, citric acid, benzoic acid and ascorbic acid.

The 2-(1-oxo-1H-isoquinolin-2-yl)acetamide derivatives of the present invention exist in both solvated and unsolvated forms, including hydrated forms. These forms are also encompassed within the scope of the present invention.

The 2-(1-oxo-1H-isoquinolin-2-yl)acetamide derivatives of the present invention also exist as amorphous forms. Multiple crystalline forms are also possible. All these physical forms are included within the scope of the present invention.

In a further aspect, the 2-(1-oxo-1H-isoquinolin-2-yl)acetamide derivatives of the present invention and their pharmaceutically acceptable salts and solvates are useful in therapy. As such the compounds of the present invention are useful for the manufacture of a medicament for the treatment or prevention of diseases influenced by modulation of the activity of the HPA axis. In particular the compounds are useful for the manufacture of a medicament for the treatment of schizophrenia, anxiety, hot flushes, addiction, anorexia nervosa, stress-related disorders and Alzheimer's dementia.

In a further aspect, the 2-(1-oxo-1H-isoquinolin-2-yl)acetamide derivatives of the present invention are useful for the manufacture of a medicament for the treatment or prevention of depression. Depression states in the treatment of which the compounds of the present invention and their pharmaceutically acceptable salts and solvates are particularly useful are those classified as mood disorders in the *Diagnostic and Statistical Manual of Mental Disorders, Fourth Edition—Text Revised*, American Psychiatric Association, Washington D.C. (2000), including mood episodes, depressive disorders, bipolar disorders and other mood disorders.

The present invention further includes a method for the treatment of a mammal, including a human, suffering from or liable to suffer from depression or any of the aforementioned disorders, which comprises administering an effective amount of a 2-(1-oxo-1H-isoquinolin-2-yl)acetamide derivative of the present invention or a pharmaceutically acceptable salt or solvate thereof.

The amount of a 2-(1-oxo-1H-isoquinolin-2-yl)acetamide derivative of the present invention or a pharmaceutically acceptable salt or solvate thereof, also referred to herein as the active ingredient, which is required to achieve a therapeutic effect will, of course, vary with the particular compound, the route of administration, the age and condition of the recipient, and the particular disorder or disease being treated.

A suitable daily dose for any of the above mentioned disorders will be in the range of 0.001 to 50 mg per kilogram body weight of the recipient (e.g. a human) per day, preferably in the range of 0.01 to 20 mg per kilogram body weight per day. The desired dose may be presented as multiple sub-doses administered at appropriate intervals throughout the day.

Whilst it is possible for the active ingredient to be administered alone, it is preferable to present it as a pharmaceutical formulation. The present invention therefore also provides a pharmaceutical composition comprising a 2-(1-oxo-1H-isoquinolin-2-yl)acetamide derivative according to the present invention in admixture with one or more pharmaceutically acceptable auxiliaries, such as the ones described in Gennaro et. al., Remmington: *The Science and Practice of Pharmacy*, $20^{th}$ Edition, Lippincott, Williams and Wilkins, 2000; see especially part 5: pharmaceutical manufacturing. Suitable auxiliaries are described e.g., in the Handbook of Pharmaceutical Excipients, $2^{nd}$ Edition; Editors A. Wade and P. J. Weller, American Pharmaceutical Association, Washington, The Pharmaceutical Press, London, 1994. Compositions include those suitable for oral, nasal, topical (including buccal, sublingual and transdermal), parenteral (including subcutaneous, intravenous and intramuscular) or rectal administration.

The mixtures of a 2-(1-oxo-1H-isoquinolin-2-yl)acetamide derivative according to the present invention and one or more pharmaceutically acceptable auxiliary or auxiliaries may be compressed into solid dosage units, such as tablets, or be processed into capsules or suppositories. By means of pharmaceutically suitable liquids the 2-(1-oxo-1H-isoquinolin-2-yl)acetamide derivatives can also be applied as an injection preparation in the form of a solution, suspension, emulsion, or as a spray, e.g., a nasal or buccal spray. For making dosage units e.g., tablets, the use of conventional additives such as fillers, colorants, polymeric binders and the like is contemplated. In general, any pharmaceutically acceptable additive can be used. The 2-(1-oxo-1H-isoquinolin-2-yl)acetamide derivatives of the invention are also suitable for use in an implant, a patch, a gel or any other preparation for immediate and/or sustained release.

Suitable fillers with which the pharmaceutical compositions can be prepared and administered include lactose, starch, cellulose and derivatives thereof, and the like, or mixtures thereof used in suitable amounts.

The following Examples further illustrate the compounds of the present invention and methods for their synthesis. In the following section, there is described the synthesis of precursors and common intermediates for compounds of the present invention.

Procedure I

INTERMEDIATE I.1:
2-Amino-N-isopropylacetamide

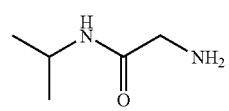

a) (Isopronylcarbamoylmethyl)carbamic acid benzyl ester

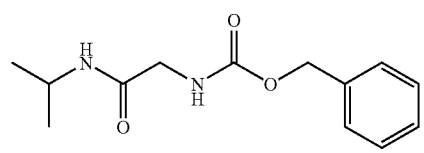

To a solution of N-Cbz-glycine (20.9 g, 100 mmol) in THF (400 mL) at 0° C. was added N-methylmorpholine (NMM) (12.1 mL, 110 mmol) and i-butylchloroformate (13 mL, 100 mmol). The resultant mixture was stirred at 0° C. for 2 min and then i-propylamine (9.4 mL, 110 mmol) was added. The reaction mixture was warmed to room temperature and stirred at this temperature for 16 h. The mixture was filtered through a pad of Celite and concentrated in vacuo. The crude residue was dissolved in ethyl acetate (500 mL) and washed with 1 N HCl (aq.) (1×100 mL), sat. NaHCO₃ (aq.) (1×100 mL) and brine (1×100 mL). The organic layer was dried (MgSO₄), filtered and concentrated in vacuo to afford (isopropylcarbamoylmethyl)carbamic acid benzyl ester (24.5 g, 98 mmol, 98%) as a white solid which was used without further purification in the next reaction.

Data for (isopropylcarbamoylmethyl)carbamic acid benzyl ester ¹H NMR (300 MHz, CDCl₃): δ 7.37 (m, 5H), 5.78 (br s, 1H), 5.41 (br s, 1H), 5.15 (s, 2H), 4.07 (septet, 1H), 3.82 (d, 2H), 1.15 (d, 6H) ppm.

b) 2-Amino-N-isopropylacetamide

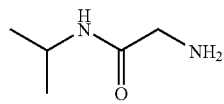

10% Pd/C (425 mg) was added to a solution of (isopropylcarbamoylmethyl)carbamic acid benzyl ester (10 g, 40 mmol) in EtOH (200 mL) and shaken under 50 p.s.i. H₂ (g) in a Parr shaker for 16 h. The reaction mixture was filtered through a pad of Celite and the solvent removed in vacuo. This afforded 2-amino-N-isopropylacetamide (INTERMEDIATE I.1) as a clear, colourless oil (5.1 g, 40 mmol, 100%).

Data for 2-amino-N-isopropylacetamide (INTERMEDIATE I.1): ¹H NMR (300 MHz, CDCl₃): δ 7.05 (brs, 1H), 4.11 (septet, 1H), 3.33 (s, 2H), 1.48 (brs, 2H, amine NH₂), 1.15 (d, 6H) ppm.

Similarly prepared was:
INTERMEDIATE I.2: 2-Amino-N-tert-butylacetamide

Procedure II

INTERMEDIATE II.1:
1-Fluoro-2-methoxy-4-vinylbenzene

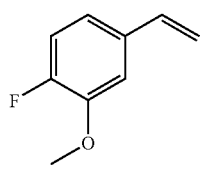

To a stirred suspension of methyltriphenylphosphonium bromide (68.20 g, 0.191 mol) in anhydrous THF (400 mL) cooled to −40° C. was added n-butyllithium (2.5 M in hexanes, 71.2 mL, 0.178 mol) via syringe over 15 min, at which point the characteristic yellow color of the phosphorus ylide persisted. The reaction mixture was warmed to −10° C. over 1 h to complete the reaction. The mixture was subsequently cooled to −30° C. and a solution of 4-fluoro-3-methoxybenzaldehyde (10.00 g, 63.64 mmol) in anhydrous THF (40 mL) was added via a cannula over 10 min. The resultant mixture was warmed to ambient temperature over 16 h. The reaction was quenched by gradual addition of water (200 mL) and the aqueous extracted with diethyl ether (3×200 mL). The combined organic layers were washed with water (2×200 mL), brine (200 mL), dried (MgSO₄) and concentrated under reduced pressure to give 1-fluoro-2-methoxy-4-vinylbenzene (INTERMEDIATE II.1) (8.69 g, 57.1 mmol, 90%) as a yellow oil.

Data for 1-fluoro-2-methoxy-4-vinylbenzene (INTERMEDIATE II.1): ¹H NMR (300 MHz, CDCl₃): δ 7.05-6.90 (m, 3H), 6.67 (dd, 1H), 5.67 (d, 1H), 5.24 (d, 1H), 3.92 (s, 3H) ppm.

Similarly prepared were:
INTERMEDIATE II.2: 2-methoxy-6-vinylpyridine (from 6-methoxypicolinaldehyde)
INTERMEDIATE II.3: 1-chloro-2-fluoro-5-vinylbenzene (from 3-chloro-4-fluorobenzaldehyde)

Procedure III: Method A

INTERMEDIATE III.1: N-tert-Butyl-2-[3-(4-fluoro-3-methoxyphenyl)-7-hydroxy-1-oxo-1H-isoquinolin-2-yl]acetamide

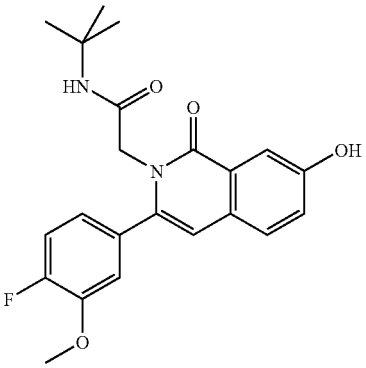

a) 2-Iodo-5-(4-methoxybenzyloxy)benzoic acid 4-methoxybenzyl ester

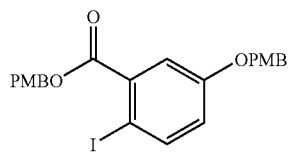

To a stirred solution of 2-iodo-5-hydroxybenzoic acid (prepared according to the method described in *J. Am. Chem. Soc.*, 1984, 106, 2651) (27.15 g, 103 mmol) in anhydrous acetonitrile (400 mL) was added cesium carbonate (73.80 g, 227 mmol) and 4-methoxybenzyl chloride (33.5 mL, 247 mmol). The resulting solid mass was broken up and the mixture heated at 65° C. for 15 h. The reaction mixture was poured into sat. NaHCO₃ (aq.) (400 mL) and the resultant mixture extracted with ethyl acetate (3×300 mL). The combined organic extracts were washed with brine (300 mL), dried (MgSO₄) and concentrated in vacuo. The crude product was purified by chromatography on silica gel with a gradient of ethyl acetate:hexanes (1:9, v/v) to ethyl acetate:hexanes (1:3, v/v) as eluent to afford 2-iodo-5-(4-methoxybenzyloxy)benzoic acid 4-methoxybenzyl ester (15.39 g, 30.52 mmol, 30%).

Data for 2-iodo-5-(4-methoxybenzyloxy)benzoic acid 4-methoxybenzyl ester: $^1$H NMR (400 MHz, (CD$_3$)$_2$SO): δ 7.81 (d, 1H), 7.39 (d, 2H), 7.32 (d, 2H), 7.27 (d, 1H), 6.95-6.84 (m, 5H), 5.21 (s, 2H), 5.01 (s, 2H), 3.73 (s, 3H), 3.71 (s, 3H) ppm.

b) (E)-2-[2-(4-Fluoro-3-methoxyphenyl)vinyl]-5-(4-methoxybenzyloxy)benzoic acid 4-methoxybenzyl ester

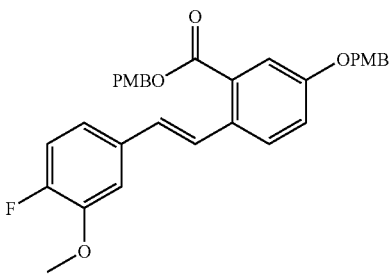

To a stirred solution of 1-fluoro-2-methoxy-4-vinylbenzene (INTERMEDIATE I.1) (4.49 g, 29.53 mmol) and 2-iodo-5-(4-methoxybenzyloxy)benzoic acid 4-methoxybenzyl ester (14.89 g, 29.53 mmol) in anhydrous acetonitrile (75 mL) was added triethylamine (8.2 mL, 59.06 mmol) and tri(o-tolyl)phosphine (1.17 g, 3.84 mmol). The mixture was sparged for 5 min with argon, and palladium(II) acetate (662 mg, 2.95 mmol) was added. The mixture was heated at reflux for 13 h and concentrated to give the crude product (E)-2-[2-(4-fluoro-3-methoxyphenyl)vinyl]-5-(4-methoxybenzyloxy)benzoic acid 4-methoxybenzyl ester as a dark brown residue, which was used without further purification.

c) (E)-2-[2-(4-Fluoro-3-methoxyphenyl)vinyl]-5-(4-methoxybenzyloxy)benzoic acid

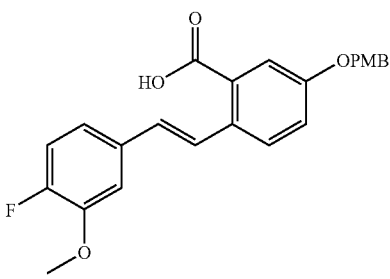

To a stirred suspension of crude (E)-2-[2-(4-fluoro-3-methoxyphenyl)vinyl]-5-(4-methoxybenzyloxy)benzoic acid 4-methoxybenzyl ester in MeOH:THF:H$_2$O (3:1:1 v/v, 150 mL) was added lithium hydroxide monohydrate (4.95 g, 118 mmol). The resultant suspension was stirred for 15 h at ambient temperature, then concentrated in vacuo. The residue was taken up in H$_2$O (500 mL), and the solution was extracted with ethyl acetate (2×200 mL). The aqueous phase was acidified to pH 2 with conc. HCl, and the mixture was extracted with ethyl acetate (3×200 mL), dried (MgSO$_4$) and concentrated in vacuo to give (E)-2-[2-(4-fluoro-3-methoxyphenyl)vinyl]-5-(4-methoxybenzyloxy)benzoic acid (8.75 g, 21.4 mmol, 73% from 2-iodo-5-(4-methoxybenzyloxy)benzoic acid 4-methoxybenzyl ester as a light brown powder.

d) 3-(4-Fluoro-3-methoxyphenyl)-7-(4-methoxybenzyloxy)isochromen-1-one

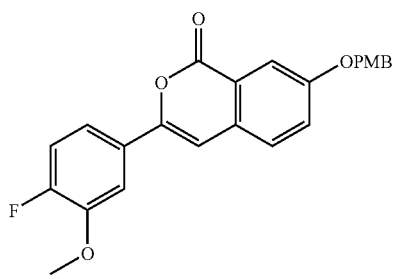

A solution of (E)-2-[2-(4-fluoro-3-methoxyphenyl)vinyl]-5-(4-methoxybenzyloxy)benzoic acid (600 mg, 1.47 mmol) in anhydrous THF (5 mL) was sparged with nitrogen for 5 min, then PdCl$_2$(MeCN)$_2$ (39 mg, 0.15 mmol), p-benzoquinone (175 mg, 1.62 mmol), and molecular sieves (10 mg) were added and the mixture stirred at room temperature for 24 h. The reaction mixture was diluted with ethyl acetate and washed with 1 N NaOH (aq.). The organic layer was washed with brine, dried (MgSO$_4$) and concentrated in vacuo. The crude residue was purified by chromatography on silica gel with hexanes:EtOAc (2:1, v/v) as eluent to afford 3-(4-fluoro-3-methoxyphenyl)-7-(4-methoxybenzyloxy)isochromen-1-one (300 mg, 0.74 mmol, 50%).

Data for 3-(4-fluoro-3-methoxyphenyl)-7-(4-methoxybenzyloxy)isochromen-1-one: $^1$H NMR (400 MHz, CDCl$_3$): δ 7.80 (d, 1H), 7.46-7.35 (m, 6H), 7.13 (dd, 1H), 6.94 (d, 2H), 6.86 (s, 1H), 5.09 (s, 2H), 3.98 (s, 3H), 3.82 (s, 3H) ppm.

e) N-tert-Butyl-2-(3-(4-fluoro-3-methoxyphenyl)-7-(4-methoxybenzyloxy)-1-oxo-1H-isoquinolin-2-yl)acetamide

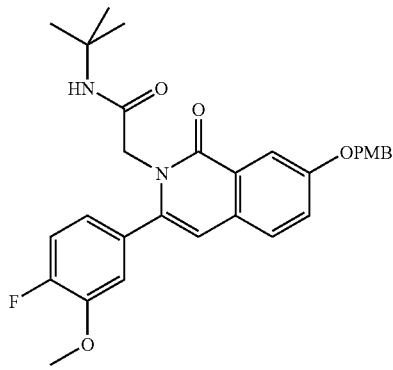

A neat mixture of 3-(4-fluoro-3-methoxyphenyl)-7-(4-methoxybenzyloxy)isochromen-1-one (100 mg, 0.25 mmol) and 2-amino-N-tert-butyl acetamide (INTERMEDIATE I.2) (32 mg, 2.46 mmol) was heated at 120° C. for 3 h. The reaction mixture was cooled and partitioned between ethyl acetate and sat. NH$_4$Cl (aq.). The organic layer was washed with brine (1×20 mL), dried (MgSO$_4$) and concentrated in vacuo to afford N-tert-butyl-2-(3-(4-fluoro-3-methoxyphenyl)-7-(4-methoxybenzyloxy)-1-oxo-1H-isoquinolin-2-yl)acetamide (120 mg, 0.23 mmol, 94%) which was used in the next step without further purification.

Data for N-tert-butyl-2-(3-(4-fluoro-3-methoxyphenyl)-7-(4-methoxybenzyloxy)-1-oxo-1H-isoquinolin-2-yl)acetamide: MS (ESI) m/z: 519 ([M+H]$^+$).

f) N-tert-Butyl-2-(3-(4-fluoro-3-methoxyphenyl)-7-hydroxy-1-oxo-1H-isoquinolin-2-yl)acetamide (INTERMEDIATE III.1)

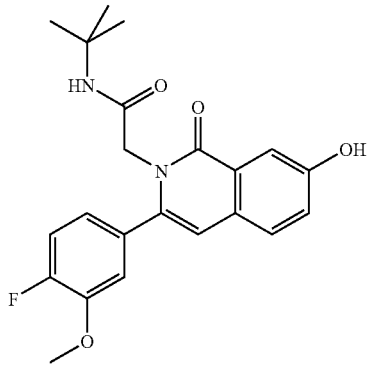

N-tert-Butyl-2-(3-(4-fluoro-3-methoxyphenyl)-7-(4-methoxybenzyloxy)-1-oxo-1H-isoquinolin-2-yl)acetamide (120 mg, 0.231 mmol) was treated with TFA:DCM (1:1 v/v, 5 mL) and stirred at room temperature for 1 h. The mixture was concentrated in vacuo and the crude residue was purified by preparative HPLC giving N-tert-butyl-2-(3-(4-fluoro-3-methoxyphenyl)-7-hydroxy-1-oxo-1H-isoquinolin-2-yl)acetamide (INTERMEDIATE III.1) (25 mg, 0.063 mmol, 27%).

Data for N-tert-butyl-2-(3-(4-fluoro-3-methoxyphenyl)-7-hydroxy-1-oxo-1H-isoquinolin-2-yl)acetamide (INTERMEDIATE III.1): MS (ESI) m/z: 399 ([M+H]$^+$).

Similarly prepared were:

INTERMEDIATE III.2: 2-[3-(4-Fluoro-3-methoxyphenyl)-7-hydroxy-1-oxo-1H-isoquinolin-2-yl]-N-isopropylacetamide (from INTERMEDIATE II.1 & INTERMEDIATE I.1)

INTERMEDIATE III.3: 2-[7-Hydroxy-3-(3-methoxyphenyl)-1-oxo-1H-isoquinolin-2-yl]-N-isopropylacetamide (from INTERMEDIATE I.1 and 3-methoxystyrene)

INTERMEDIATE III.4: N-tert-Butyl-2-[7-hydroxy-3-(3-methoxyphenyl)-1-oxo-1H-isoquinolin-2-yl]acetamide (from INTERMEDIATE I.2 and 3-methoxystyrene)

INTERMEDIATE III.5: 2-[7-Hydroxy-3-(6-methoxypyridin-2-yl)-1-oxo-1H-isoquinolin-2-yl]-N-isopropylacetamide (from INTERMEDIATE II.2 & INTERMEDIATE I.1)

INTERMEDIATE III.6: N-tert-Butyl-2-[7-hydroxy-3-(6-methoxypyridin-2-yl)-1-oxo-1H-isoquinolin-2-yl]acetamide (from INTERMEDIATE II.2 & INTERMEDIATE I.2)

Procedure III: Method B

INTERMEDIATE III.7: 2-[3-(3-Chlorophenyl)-7-hydroxy-1-oxo-1H-isoquinolin-2-yl]-N-isopropylacetamide

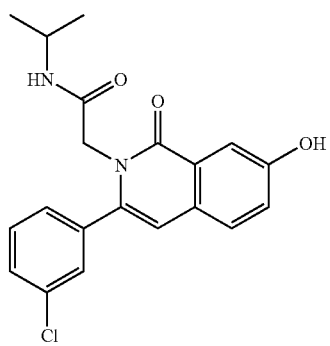

a) 2-[(E)-2-(3-Chlorophenyl)vinyl]-5-methoxybenzoic acid methyl ester

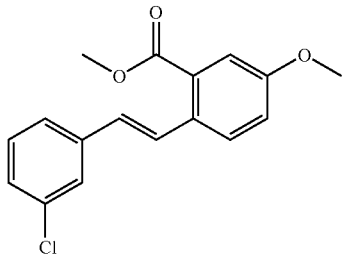

To a stirred solution of 2-bromo-5-methoxybenzoic acid methyl ester (17.7 g, 72.2 mmol) and 3-chlorovinylbenzene (9.17 mL, 72.2 mmol) in anhydrous acetonitrile (180 mL) was added triethylamine (20.10 mL, 144 mmol) and tris(o-tolyl)phosphine (2.85 g, 9.38 mmol). The reaction mixture was sparged with argon for 5 min, palladium(II) acetate (1.62 g, 7.22 mmol) was added and the mixture heated at 85° C. under an argon atmosphere for 21 h. The product mixture was filtered through celite, concentrated in vacuo, the residue dissolved in ethyl acetate (400 mL) and washed with 1 N HCl (aq.) (200 mL) and brine (200 mL). The combined aqueous layers were back-extracted with ethyl acetate (200 mL). The ethyl acetate extracts were combined, dried (MgSO$_4$) and concentrated under reduced pressure to give the crude 2-[(E)-2-(3-chlorophenyl)vinyl]-5-methoxybenzoic acid methyl ester as a red-brown, viscous oil which was used in the next step without further purification.

Data for 2-[(E)-2-(3-chlorophenyl)vinyl]-5-methoxybenzoic acid methyl ester: $^1$H NMR (300 MHz, CDCl$_3$): δ 7.91 (d, 1H), 7.63 (d, 1H), 7.49 (dd, 1H), 7.44 (d, 1H), 7.41 (ddd, 1H), 7.26 (d, 1H), 7.21 (ddd, 1H), 7.08 (dd, 1H), 6.83 (d, 1H), 3.94 (s, 3H), 3.86 (s, 3H) ppm.

b) (E)-2-[2-(3-Chlorophenyl)vinyl]-5-methoxybenzoic acid

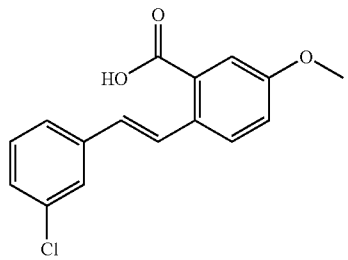

Crude 2-[(E)-2-(3-chlorophenyl)vinyl]-5-methoxybenzoic acid methyl ester was suspended in methanol:THF:water (3:1:1 [v/v], 400 mL) and lithium hydroxide (12.10 g, 289 mmol) added. The mixture was stirred for 22 h at ambient temperature and concentrated in vacuo to give a pale brown solid. The crude product was re-dissolved in water (400 mL), the solution washed with diethyl ether (3×250 mL) and acidified to pH 2 with 1 N HCl (aq.). The aqueous was extracted with ethyl acetate (3×200 mL), the organic phase dried (MgSO$_4$) and concentrated in vacuo to give a tan solid which was triturated with methanol and filtered to give (E)-2-[2-(3-chlorophenyl)vinyl]-5-methoxybenzoic acid (15.43 g, 53.44 mmol, 74% for 2 steps from 2-bromo-5-methoxybenzoic acid methyl ester) as an off-white powder.

Data for (E)-2-[2-(3-chlorophenyl)vinyl]-5-methoxybenzoic acid: $^1$H NMR (300 MHz, (CD$_3$)$_2$SO): δ 7.87 (d, 1H), 7.76 (d, 1H), 7.56 (dd, 1H), 7.49 (ddd, 1H), 7.40 (app t, 1H), 7.35 (d, 1H), 7.32 (ddd, 1H), 7.17 (dd, 1H), 7.05 (d, 1H), 3.82 (s, 3H) ppm.

c) 3-(3-Chlorophenyl)-7-methoxyisochromen-1-one

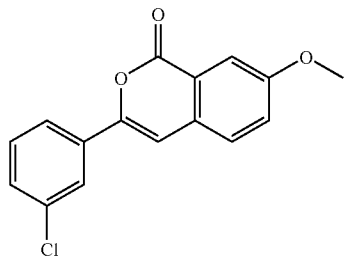

A solution of (E)-2-[2-(3-chlorophenyl)vinyl]-5-methoxybenzoic acid (15.00 g, 51.95 mmol) in anhydrous THF (520 mL) was sparged with argon for 5 min. p-Benzoquinone (6.18 g, 57.20 mmol) was added followed by bis(acetonitrile)dichloropalladium(II) (674 mg, 2.60 mmol) and the resultant mixture stirred at ambient temperature for 17 h. 1 N NaOH (aq.) (375 mL) was added and the resultant brown solid washed with chloroform (4×200 mL) to provide 3-(3-chlorophenyl)-7-methoxyisochromen-1-one (10.96 g, 38.23 mmol, 74%) as pale yellow solid.

Data for 3-(3-chlorophenyl)-7-methoxyisochromen-1-one: $^1$H NMR (300 MHz, CDCl$_3$): δ 7.86-7.84 (m, 1H), 7.75-7.72 (m, 2H), 7.45 (d, 1H), 7.43-7.36 (m, 2H), 7.33 (dd, 1H), 6.94 (s, 1H), 3.93 (s, 3H) ppm; MS (ESI) m/z: 287 ([M+H]$^+$).

d) 2-[3-(3-Chlorophenyl)-7-methoxy-1-oxo-1H-isoquinolin-2-yl]-N-isopropylacetamide

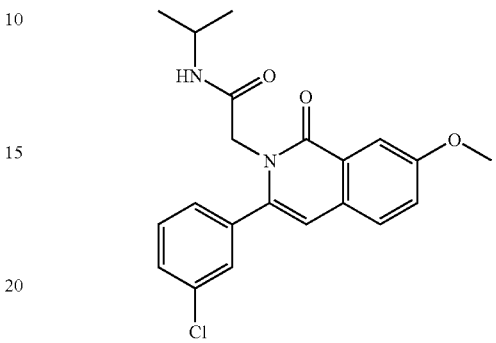

In an open, 50 mL two-necked round bottom flask, a neat mixture of compound 3-(3-chlorophenyl)-7-methoxyisochromen-1-one (1.00 g, 3.49 mmol) and 2-amino-N-isopropylacetamide (INTERMEDIATE I.1) (2.02 g, 17.4 mmol, 5 eq) was heated to 120° C. under argon for 3 days, adding absolute EtOH in aliquots (2 mL) daily to loosen up the reaction mixture. The residue was purified by chromatography on silica gel with ethyl acetate:hexane (1:3, v/v) as eluent to give 2-[3-(3-chlorophenyl)-7-methoxy-1-oxo-1H-isoquinolin-2-yl]-N-isopropylacetamide (0.985 g, 2.56 mmol, 73%) as a white solid.

Data for 2-[3-(3-chlorophenyl)-7-methoxy-1-oxo-1H-isoquinolin-2-yl]-N-isopropylacetamide: $^1$H NMR (300 MHz, CDCl$_3$): δ 7.82 (d, 1H), 7.47-7.37 (m, 5H), 7.29 (dd, 1H), 6.47 (s, 1H), 5.87 (br d, 1H), 4.45 (s, 2H), 4.06 (septet, 1H), 3.94 (s, 3H), 1.15 (d, 6H) ppm; MS (ESI) m/z: 326 ([M–C$_3$H$_8$N]$^+$), 385 ([M+H]$^+$).

e) 2-[3-(3-Chlorophenyl)-7-hydroxy-1-oxo-1H-isoquinolin-2-yl]-N-isopropylacetamide (INTERMEDIATE III.7)

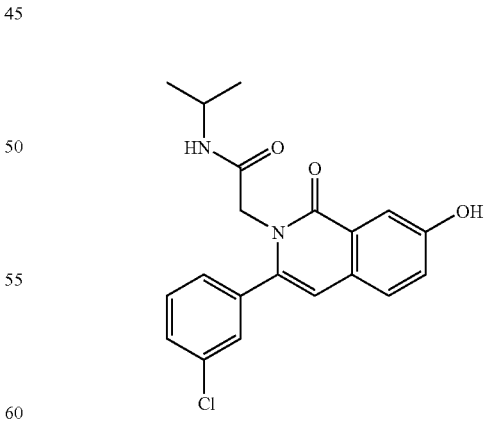

A solution of 2-[3-(3-chlorophenyl)-7-methoxy-1-oxo-1H-isoquinolin-2-yl]-N-isopropylacetamide (886 mg, 2.30 mmol) in dry DCM (25 mL) was cooled to −78° C. and a solution of BBr$_3$ (1 M in DCM, 20.3 mL, 20.3 mmol) was added dropwise. After 1 h, the cooling bath was removed and the mixture was allowed to stir an additional 17.5 h, then cooled to 0° C. and quenched by dropwise addition of sat. NaHCO₃ (aq.) (15 mL). The aqueous mixture was extracted with IPA:DCM (1:3, v/v) (4×25 mL). The combined organic extracts were washed with brine (25 mL), dried (MgSO₄) and concentrated to give the crude product, which was recrystallized from EtOH to give pure 2-[3-(3-chlorophenyl)-7-hydroxy-1-oxo-1H-isoquinolin-2-yl]-N-isopropylacetamide (INTERMEDIATE III.7) (530 mg, 1.43 mmol, 62%) as white solid.

Data for 2-[3-(3-chlorophenyl)-7-hydroxy-1-oxo-1H-isoquinolin-2-yl]-N-isopropylacetamide (INTERMEDIATE III.7): ¹H NMR (300 MHz, d⁶-DMSO): δ 10.02 (s, 1H), 7.83 (d, 1H), 7.55-7.39 (m, 5H), 7.42-7.39 (m, 1H), 7.21 (dd, 1H), 6.49 (s, 1H), 4.33 (s, 2H), 3.77 (septet, 1H), 0.99 (d, 6H) ppm; MS (ESI) m/z: 312 ([M–C₃H₈N]⁺), 371 ([M+H]⁺), 763 ([2M+Na]⁺).

Similarly prepared were:

INTERMEDIATE III.8: N-tert-Butyl-2-[3-(3-chlorophenyl)-7-hydroxy-1-oxo-1H-isoquinolin-2-yl]acetamide (from INTERMEDIATE I.2 and 3-chlorostyrene)

INTERMEDIATE III.9: 2-[3-(3-Fluorophenyl)-7-hydroxy-1-oxo-1H-isoquinolin-2-yl]-N-isopropylacetamide (from INTERMEDIATE I.1 and 3-fluorostyrene)

INTERMEDIATE III.10: 2-(7-Hydroxy-1-oxo-3-phenyl-1H-isoquinolin-2-yl)-N-isopropylacetamide (from INTERMEDIATE I.1 and styrene)

INTERMEDIATE III.11: N-tert-Butyl-2-[3-(3-chloro-4-fluorophenyl)-7-hydroxy-1-oxo-1H-isoquinolin-2-yl]acetamide (from INTERMEDIATE II.3 & INTERMEDIATE I.2)

SYNTHESIS OF EXAMPLES ACCORDING TO THE INVENTION

Example 1

2-[3-(3-Chlorophenyl)-7-((S)-2-methyl-3-pyrrolidin-1-ylpropoxy)-1-oxo-1H-isoquinolin-2-yl]-N-isopropylacetamide

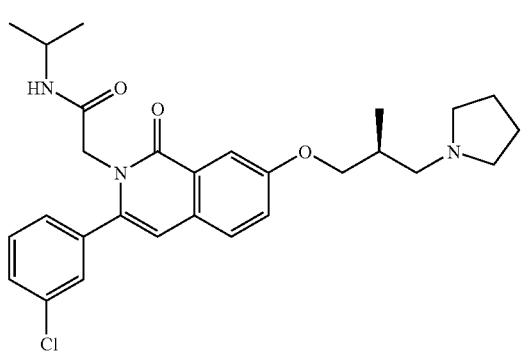

a) 2-[3-(3-Chlorophenyl)-7-((S)-3-hydroxy-2-methylpropoxy)-1-oxo-1H-isoquinolin-2-yl]-N-isopropylacetamide

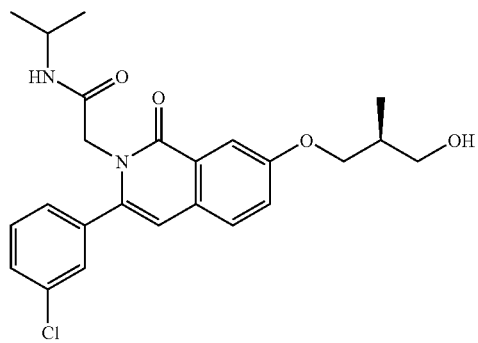

A suspension of 2-[3-(3-chlorophenyl)-7-hydroxy-1-oxo-1H-isoquinolin-2-yl]-N-isopropylacetamide (INTERMEDIATE III.7) (347 mg, 0.936 mmol), K₂CO₃ (674 mg, 4.68 mmol) and (S)-(+)-3-bromo-2-methyl-1-propanol (0.48 mL, 4.7 mmol) in dry acetonitrile (5 mL) was stirred for 18 h at 80° C. The resultant mixture was poured into H₂O (20 mL), cooled to 0° C. and filtered. The precipitate was washed with cold H₂O and dried in vacuo to furnish 2-[3-(3-chlorophenyl)-7-((S)-3-hydroxy-2-methylpropoxy)-1-oxo-1H-isoquinolin-2-yl]-N-isopropylacetamide (382 mg, 0.862 mmol, 92%) as white solid.

Data for 2-[3-(3-chlorophenyl)-7-((S)-3-hydroxy-2-methylpropoxy)-1-oxo-1H-isoquinolin-2-yl]-N-isopropylacetamide: ¹H NMR (300 MHz, d⁶-DMSO): δ 7.87 (d, 1H), 7.64 (d, 1H), −7.62 (d, 1H), 7.57-7.51 (m, 3H), 7.44 (dd, 1H), 7.38 (dd, 1H), 6.57 (s, 1 H), 4.66 (br s, 1 H), 4.37 (s, 2H), 4.09 (dd, 1H), 3.92 (dd, 1H), 3.78 (septet, 1H), 3.46-3.45 (m, 2H), 2.08-2.02 (m, 1H), 1.00 (d, 6H), 1.00 (d, 3H) ppm; MS (ESI) m/z: 384 ([M–C₃H₈N]⁺), 443 ([M+H]⁺), 907 ([2M+Na]⁺).

b) Methanesulfonic acid (R)-3-[3-(3-chlorophenyl)-2-(isopropylcarbamoylmethyl)-1-oxo-1,2-dihydroisoquinolin-7-yloxy]-2-methylpropyl ester

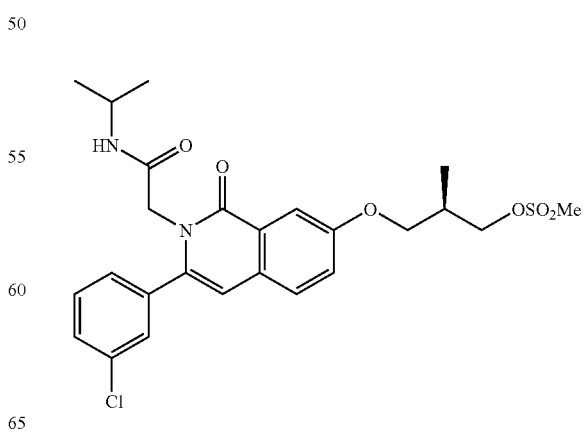

A suspension of 2-[3-(3-chlorophenyl)-7-((S)-3-hydroxy-2-methylpropoxy)-1-oxo-1H-isoquinolin-2-yl]-N-isopropylacetamide (319 mg, 0.720 mmol) and triethylamine (0.30 mL, 2.16 mmol) in dry DCM (7.0 mL) was cooled to 0° C. and methanesulfonyl chloride (67 μL, 0.86 mmol) was added dropwise via a syringe. The mixture was stirred for 1 h at 0° C., a second aliquot of methanesulfonyl chloride (25 μL, 0.32 mmol) was added, and stirring was continued 30 min at room temperature. The mixture was diluted with ethyl acetate (20 mL) and washed with 1 N HCl (aq.) (20 mL), sat. NaHCO₃ (aq.) (20 mL) and brine (20 mL). The aqueous washes were back-extracted with ethyl acetate (20 mL), and the combined organic extracts were dried (MgSO₄) and concentrated to give crude methanesulfonic acid (R)-3-[3-(3-chlorophenyl)-2-(isopropylcarbamoylmethyl)-1-oxo-1,2-dihydroisoquinolin-7-yloxy]-2-methylpropyl ester (316 mg, 0.720 mmol, 84%) as off-white solid.

Data for methanesulfonic acid (R)-3-[3-(3-chlorophenyl)-2-(isopropylcarbamoylmethyl)-1-oxo-1,2-dihydroisoquinolin-7-yloxy]-2-methylpropyl ester: ¹H NMR (300 MHz, CDCl₃): δ 7.80 (d, 1H), 7.47-7.37 (m, 5H), 7.29 (dd, 1H), 6.46 (s, 1H), 5.82 (br d, 1 H), 4.44 (s, 2 H), 4.33 (d, 2H), 4.13-4.01 (m, 3H), 3.00 (s, 3H), 2.50-2.43 (m, 1H), 1.15 (d, 6H), 1.15 (d, 3H) ppm; MS (ESI) m/z: 462 ([M−C₃H₈N]⁺), 521 ([M+H]⁺).

c) 2-[3-(3-Chlorophenyl)-7-((S)-2-methyl-3-pyrrolidin-1-ylpropoxy)-1-oxo-1H-isoquinolin-2-yl]-N-isopropylacetamide (EXAMPLE 1)

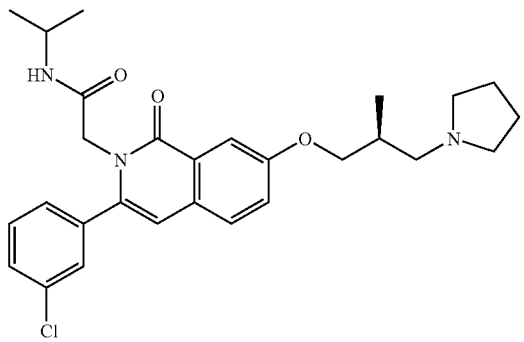

To a stirred suspension of methanesulfonic acid (R)-3-[3-(3-chlorophenyl)-2-(isopropylcarbamoylmethyl)-1-oxo-1,2-dihydroisoquinolin-7-yloxy]-2-methylpropyl ester (310 mg, 0.595 mmol) in dry acetonitrile (3 mL) was added K₂CO₃ (412 mg, 2.98 mmol) and pyrrolidine (150 mL, 1.78 mmol). The mixture was heated at reflux temperature for 6 h and water (10 mL) was added. The resultant suspension was extracted with ethyl acetate (3×25 mL), and the combined organic extracts were dried (MgSO₄) and concentrated in vacuo. Purification by chromatography on silica gel with MeOH:DCM:NH₄OH (aq.) (1:18.9:0.1 v/v) gave 2-[3-(3-chlorophenyl)-7-((S)-2-methyl-3-pyrrolidin-1-ylpropoxy)-1-oxo-1H-isoquinolin-2-yl]-N-isopropylacetamide (EXAMPLE 1) (146 mg, 0.294 mmol, 67%). Data for 2-[3-(3-chlorophenyl)-7-((S)-2-methyl-3-pyrrolidin-1-ylpropoxy)-1-oxo-1H-isoquinolin-2-yl]-N-isopropylacetamide (EXAMPLE 1): ¹H NMR (300 MHz, CDCl₃): δ 7.83 (d, 1H), 7.47-7.37 (m, 5H), 7.30 (dd, 1H), 6.46 (s, 1H), 5.91 (br d, 1H), 4.45 (s, 2H), 4.15 (dd, 1H), 4.07 (septet, 1H), 3.91 (dd, 1H), 2.62-2.46 (br m, 5H), 2.36 (dd, 1H), 2.21 (dd, 1H), 1.80-1.76 (br m, 4H), 1.16 (d, 6H), 1.11 (d, 3H) ppm; MS (ESI) m/z: 496 ([M+H]⁺), 991 ([2M+H]⁺), 1013 ([2M+Na]⁺).

The following compounds (EXAMPLES 2-14) were prepared in a similar manner from INTERMEDIATES III.

Example 2

2-[7-((S)-3-Diethylamino-2-methylpropoxy)-3-(3-fluorophenyl)-1-oxo-1H-isoquinolin-2-yl]-N-isopropylacetamide

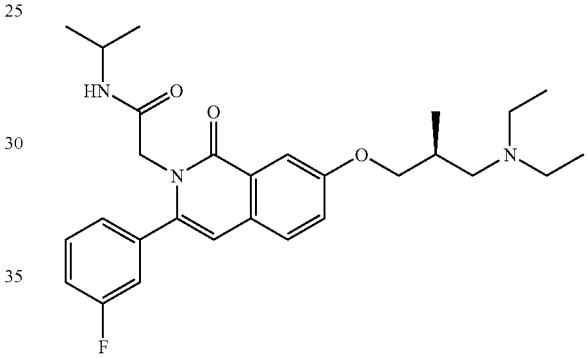

MS (ESI) m/z: 482 ([M+H]⁺) (from INTERMEDIATE III.9 & diethylamine)

Example 3

2-[7-((S)-3-Dimethylamino-2-methylpropoxy)-3-(3-fluorophenyl)-1-oxo-1H-isoquinolin-2-yl]-N-isopropylacetamide

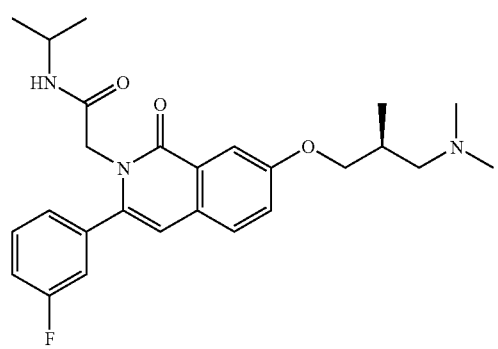

MS (ESI) m/z: 454 ([M+H]+) (from INTERMEDIATE III.9 & dimethylamine)

Example 4

2-[7-[(S)-3-(Ethylmethylamino)-2-methylpropoxy]-3-(3-methoxyphenyl)-1-oxo-1H-isoquinolin-2-yl]-N-isopropylacetamide

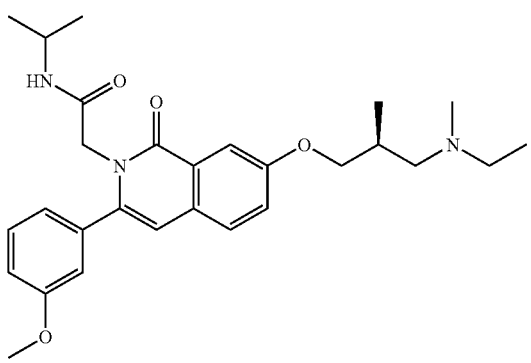

MS (ESI) m/z: 480 ([M+H]+) (from INTERMEDIATE III.3 & N-methylethylamine)

Example 5

2-[3-(3-Fluorophenyl)-7-((S)-2-methyl-3-pyrrolidin-1-ylpropoxy)-1-oxo-1H-isoquinolin-2-yl]-N-isopropylacetamide

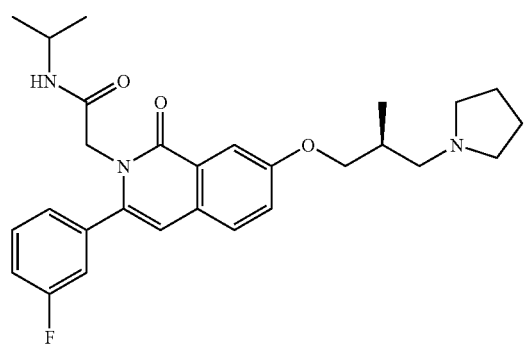

MS (ESI) m/z: 480 ([M+H]+) (from INTERMEDIATE III.9 & pyrrolidine)

Example 6

2-[3-(3-)-7-((S)-3-dimethylamino-2-methylpropoxy)-1-oxo-1H-isoquinolin-2-yl]-N-isopropylacetamide

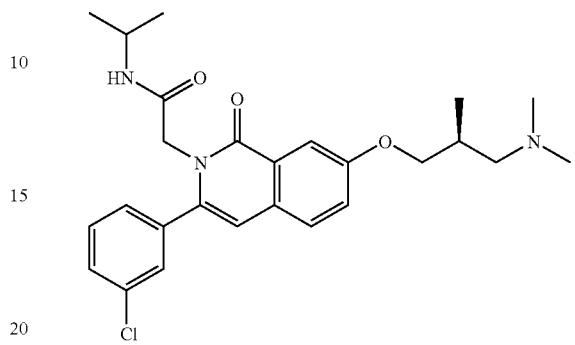

MS (ESI) m/z: 470/472 ([M+H]+) (from INTERMEDIATE III.7 & dimethylamine)

Example 7

2-[7-((S)-3-Azetidin-1-yl-2-methylpropoxy)-3-(3-methoxyphenyl)-1-oxo-1H-isoquinolin-2-yl]-N-isopropylacetamide

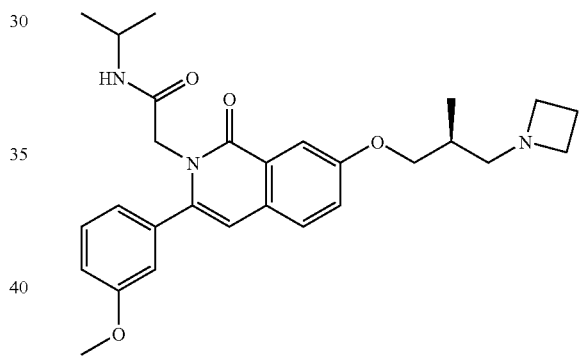

MS (ESI) m/z: 478 ([M+H]+) (from INTERMEDIATE III.3 & azetidine)

Example 8

2-[7-[(S)-3-(Isobutylmethylamino)-2-methylpropoxy]-3-(3-methoxylphenyl)-1-oxo-1H-isoquinolin-2-yl]-N-isopropylacetamide

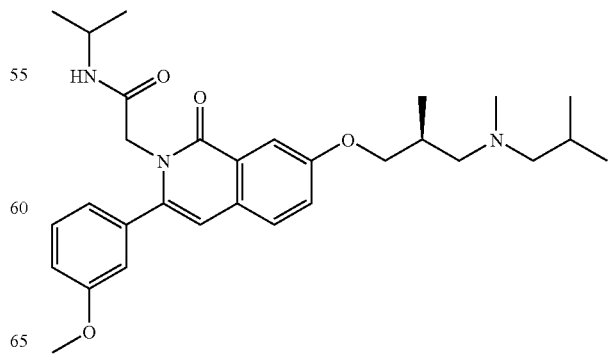

MS (ESI) m/z: 508 ([M+H]⁺) (from INTERMEDIATE III.3 & N-methylisobutylamine)

Example 9

2-[7-((S)-3-Diethylamino-2-methylpropoxy)-3-(3-methoxyphenyl)-1-oxo-1H-isoquinolin-2-yl]-N-isopropylacetamide

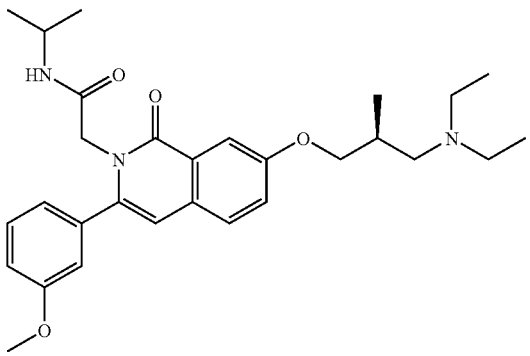

MS (ESI) m/z: 494 ([M+H]⁺) (from INTERMEDIATE III.3 & diethylamine)

Example 10

N-Isopropyl-2-[3-(3-methoxyphenyl)-7-((S)-2-methyl-3-pyrrolidin-1-ylpropoxy)-1-oxo-1H-isoquinolin-2-yl]acetamide

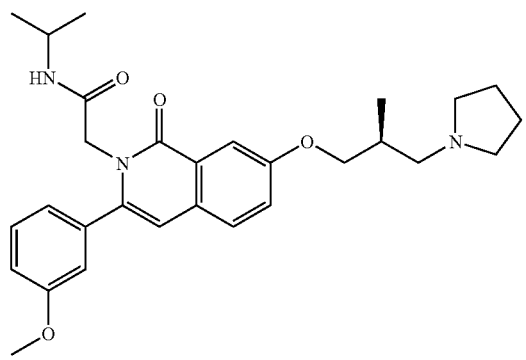

MS (ESI) m/z: 492 ([M+H]⁺) (from INTERMEDIATE III.3 & pyrrolidine)

Example 11

N-Isopropyl-2-[7-[(S)-3-(isopropylmethylamino)-2-methylpropoxy]-3-(3-methoxyphenyl)-1-oxo-1H-isoquinolin-2-yl]acetamide

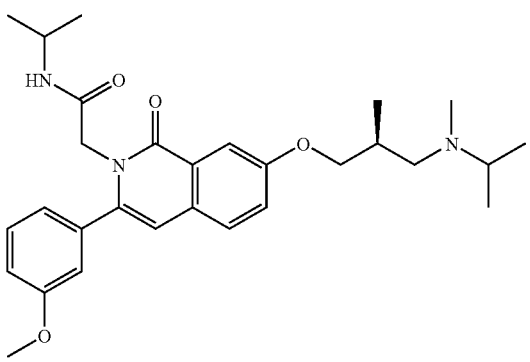

MS (ESI) m/z: 494 ([M+H]⁺) (from INTERMEDIATE III.3 & N-methylisopropylamine)

Example 12

2-[3-(3-Fluorophenyl)-7-((S)-2-methyl-3-piperidin-1-ylpropoxy)-1-oxo-1H-isoquinolin-2-yl]-N-isopropylacetamide

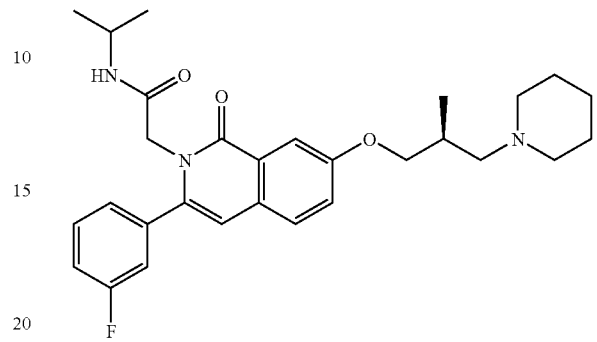

MS (ESI) m/z: 494 ([M+H]⁺) (from INTERMEDIATE III.9 & piperidine)

Example 13

2-[7-((S)-3-Dimethylamino-2-methylpropoxy)-3-(3-methoxyphenyl)-1-oxo-1H-isoquinolin-2-yl]-N-isopropylacetamide

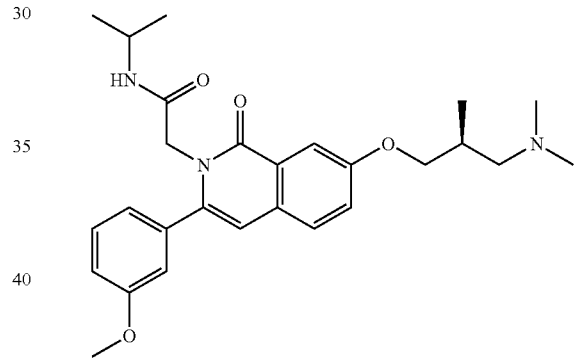

MS (ESI) m/z: 466 ([M+H]⁺) (from INTERMEDIATE III.3 & dimethylamine)

Example 14

N-Isopropyl-2-[3-(3-methoxyphenyl)-7-((S)-2-methyl-3-piperidin-1-ylpropoxy)-1-oxo-1H-isoquinolin-2-yl]acetamide

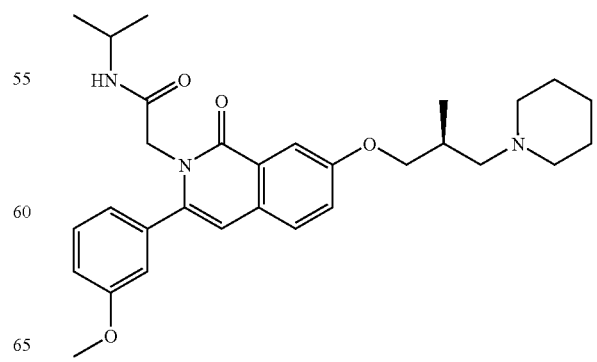

MS (ESI) m/z: 506 ([M+H]+) (from INTERMEDIATE III.3 & piperidine)

Example 15

N-tert-Butyl-2-[3-(4-fluoro-3-methoxyphenyl)-1-oxo-7-(3-pyrrolidin-1-ylpropoxy)-1H-isoquinolin-2-yl]acetamide

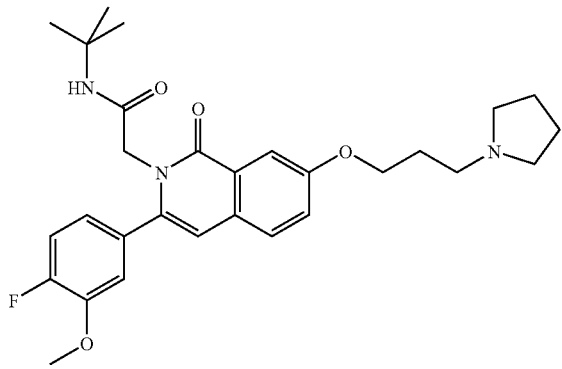

To a solution of N-tert-butyl-2-[3-(4-fluoro-3-methoxyphenyl)-7-hydroxy-1-oxo-1H-isoquinolin-2-yl]acetamide (INTERMEDIATE III.1) (25 mg, 0.063 mmol) in anhydrous acetonitrile (5 mL) were added $K_2CO_3$ (26 mg, 0.189 mmol) and 1-bromo-3-chloropropane (6.2 uL, 0.63 mmol). The reaction mixture was heated at reflux temperature for 16 h. Pyrrolidine (53 uL, 0.63 mmol) and additional $K_2CO_3$ (26 mg, 0.189 mmol) were added and the reaction mixture was heated at reflux temperature for 48 h. The reaction mixture was filtered and the filtrate concentrated in vacuo. The crude residue was purified by preparative HPLC to afford N-tert-butyl-2-[3-(4-fluoro-3-methoxyphenyl)-1-oxo-7-(3-pyrrolidin-1-ylpropoxy)-1H-isoquinolin-2-yl]acetamide (EXAMPLE 15) hydrochloride salt (4.4 mg, 0.008 mmol, 13%) as an HCl salt.

Data for N-tert-butyl-2-[3-(4-fluoro-3-methoxyphenyl)-1-oxo-7-(3-pyrrolidin-1-ylpropoxy)-1H-isoquinolin-2-yl]acetamide (EXAMPLE 15) hydrochloride salt: $^1$H NMR (400 MHz, $CD_3OD$): δ 7.76 (d, 1H), 7.62 (d, 2H), 7.38 (dd, 1H), 7.25-7.15 (m, 2H), 7.00 (m, 1H), 6.61 (s, 1H), 4.53 (s, 2H), 4.25 (t, 2H), 3.86 (s, 3H), 3.73 (m, 2H), 3.46 (m, 2H), 3.15 (m, 2H), 2.30 (m, 2H), 2.19 (m, 2H), 2.06-1.98 (m, 2H), 1.29 (s, 9H) ppm; MS (ESI) m/z: 510 ([M+H]+), 1018 ([2M+H]+).

The following compounds (EXAMPLES 16-34) were prepared in a similar manner from INTERMEDIATES III:

Example 16

2-[3-(4-Fluoro-3-methoxyphenyl)-1-oxo-7-(3-pyrrolidin-1-ylpropoxy)-1H-isoquinolin-2-yl]-N-isopropylacetamide

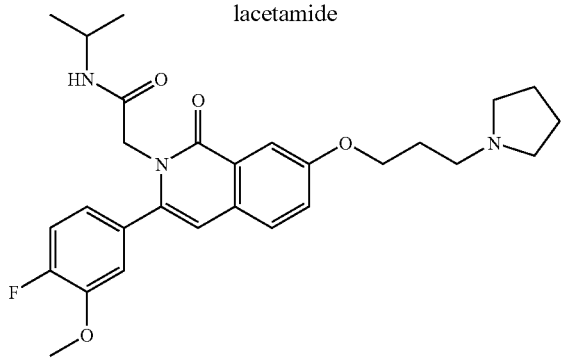

MS (ESI) m/z: 496 ([M+H]+) (from INTERMEDIATE III.2 & pyrrolidine)

Example 17

N-tert-Butyl-2-{3-(3-Chlorophenyl)-7-[3-(4-hydroxypiperidin-1-yl)-propoxy]-1-oxo-1H-isoquinolin-2-yl}-acetamide

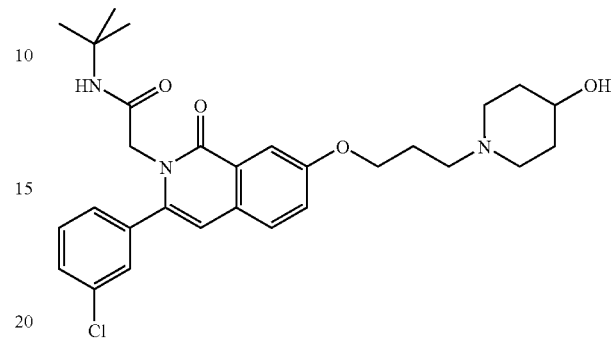

MS (ESI) m/z: 526/528 ([M+H]+) (from INTERMEDIATE III.8 & 4-hydroxypiperidine)

Example 18

N-Isopropyl-2-[3-(3-methoxyphenyl)-1-oxo-7-(3-pyrrolidin-1-ylpropoxy)-1H-isoquinolin-2-yl]-acetamide

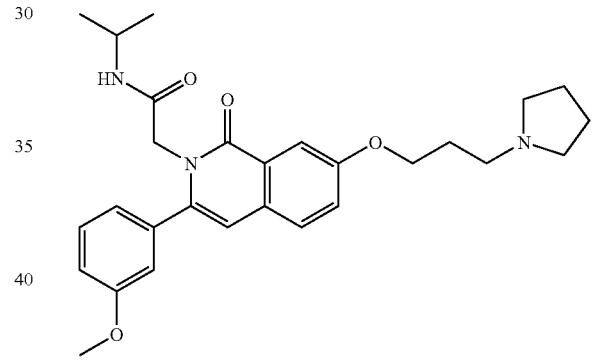

MS (ESI) m/z: 478 ([M+H]+) (from INTERMEDIATE III.3 & pyrrolidine)

Example 19

N-Isopropyl-2-[3-(3-methoxyphenyl)-1-oxo-7-(3-piperidin-1-ylpropoxy)-1H-isoquinolin-2-yl]-acetamide

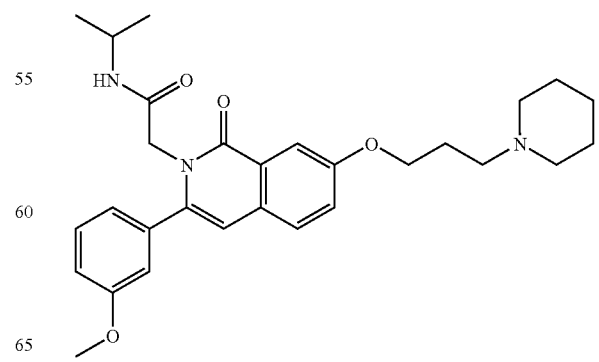

MS (ESI) m/z: 492 ([M+H]+) (from INTERMEDIATE III.3 & piperidine)

Example 20

2-[7-(3-Diethylaminopropoxy)-3-(3-methoxyphenyl)-1-oxo-1H-isoquinolin-2-yl]-N-isopropylacetamide

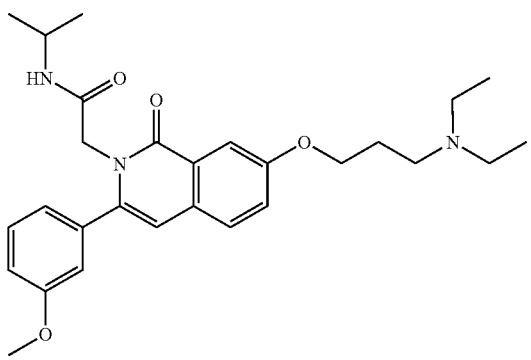

MS (ESI) m/z: 480 ([M+H]+) (from INTERMEDIATE III.3 & diethylamine)

Example 21

2-[3-(3-Chlorophenyl)-1-oxo-7-(3-piperidin-1-ylpropoxy)-1H-isoquinolin-2-yl]-N-isopropylacetamide

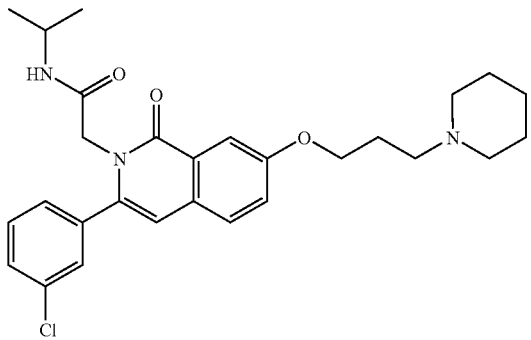

MS (ESI) m/z: 496 ([M+H]+) (from INTERMEDIATE III.7 & piperidine)

Example 22

2-[7-(3-Dimethylaminopropoxy)-3-(3-methoxyphenyl)-1-oxo-1H-isoquinolin-2-yl]-N-isopropylacetamide

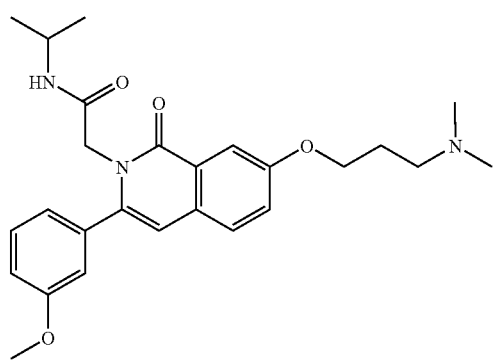

MS (ESI) m/z: 452 ([M+H]+) (from INTERMEDIATE III.3 & dimethylamine)

Example 23

N-tert-Butyl-2-[3-(6-methoxypyridin-2-yl)-1-oxo-7-(3-pyrrolidin-1-ylpropoxy)-1H-isoquinolin-2-yl]acetamide

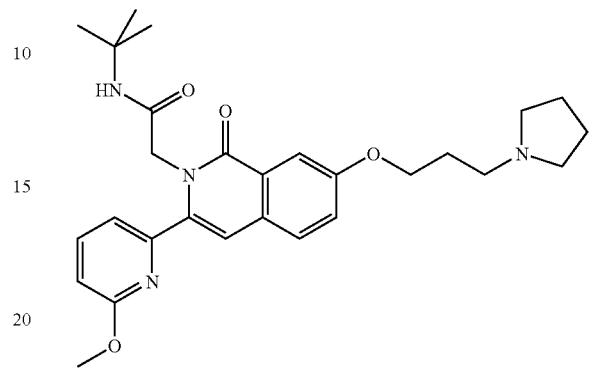

MS (ESI) m/z: 493 ([M+H]+) (from INTERMEDIATE III.6 & pyrrolidine)

Example 24

N-tert-Butyl-2-[3-(3-Chlorophenyl)-1-oxo-7-(3-pyrrolidin-1-ylpropoxy)-1H-isoquinolin-2-yl]acetamide

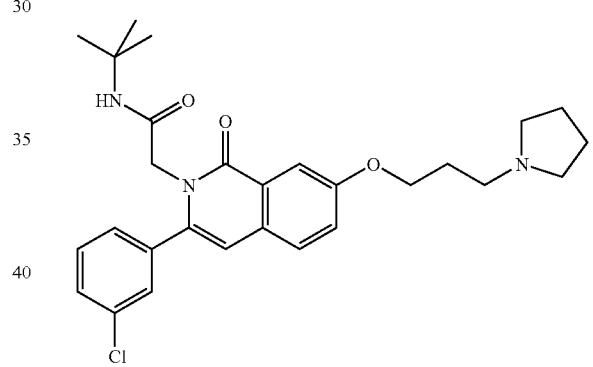

MS (ESI) m/z: 496/498 ([M+H]+) (from INTERMEDIATE III.8 & pyrrolidine)

Example 25

2-[3-(3-Chlorophenyl)-1-oxo-7-(3-pyrrolidin-1-ylpropoxy)-1H-isoquinolin-2-yl]-N-isopropylacetamide

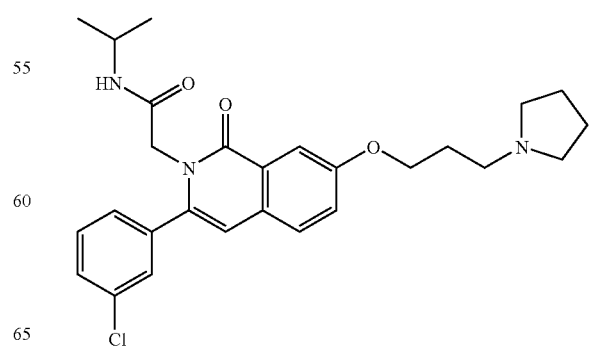

MS (ESI) m/z: 482/484 ([M+H]+) (from INTERMEDIATE III.7 & pyrrolidine)

Example 26

N-Isopropyl-2-[1-oxo-3-phenyl-7-(3-piperidin-1-ylpropoxy)-1H-isoquinolin-2-yl]acetamide

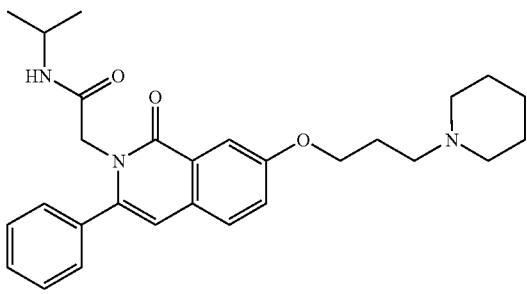

MS (ESI) m/z: 462 ([M+H]+) (from INTERMEDIATE III.10 & piperidine)

Example 27

N-tert-Butyl-2-[3-(3-chloro-4-fluorophenyl)-1-oxo-7-(3-piperidin-1-ylpropoxy)-1H-isoquinolin-2-yl]acetamide

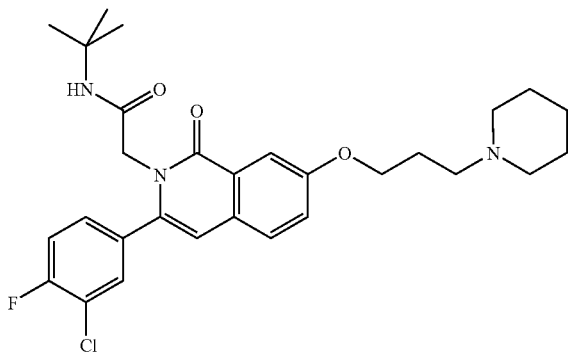

MS (ESI) m/z: 528/530 ([M+H]+) (from INTERMEDIATE III.11 & piperidine)

Example 28

N-tert-Butyl-2-[3-(3-chloro-4-fluorophenyl)-1-oxo-7-(3-pyrrolidin-1-ylpropoxy)-1H-isoquinolin-2-yl]acetamide

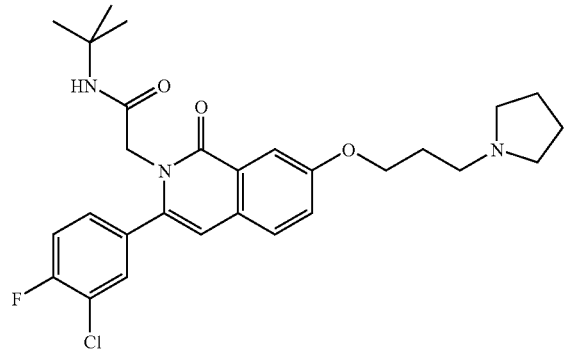

MS (ESI) m/z: 514/516 ([M+H]+) (from INTERMEDIATE III.11 & pyrrolidine)

Example 29

N-Isopropyl-2-[3-(6-methoxypyridin-2-yl)-1-oxo-7-(3-pyrrolidin-1-ylpropoxy)-1H-isoquinolin-2-yl]acetamide

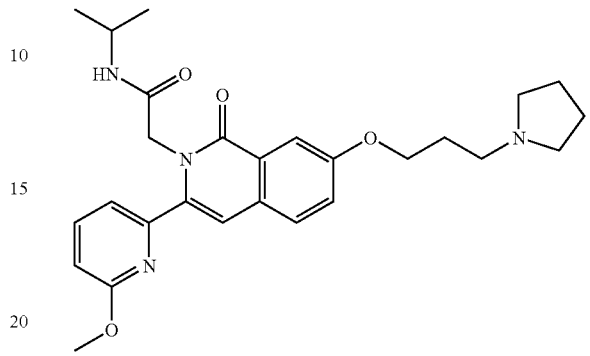

MS (ESI) m/z: 479 ([M+H]+) (from INTERMEDIATE III.5 & pyrrolidine)

Example 30

N-tert-Butyl-2-[3-(3-methoxyphenyl)-1-oxo-7-(3-pyrrolidin-1-ylpropoxy)-1H-isoquinolin-2-yl]acetamide

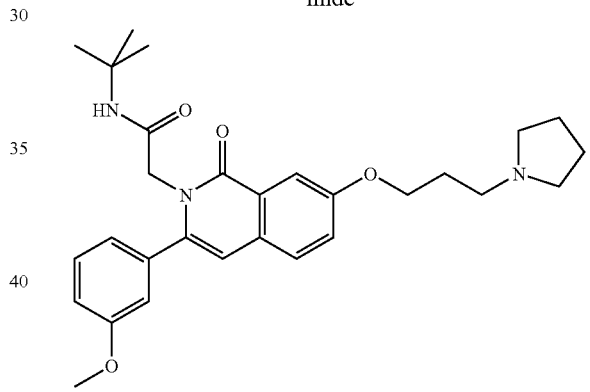

MS (ESI) m/z: 492 ([M+H]+) (from INTERMEDIATE III.4 & pyrrolidine)

Example 31

2-{3-(3-Chlorophenyl)-7-[3-(4-hydroxy-4-methylpiperidin-1-yl)-propoxy]-1-oxo-1H-isoquinolin-2-yl}-N-isopropylacetamide

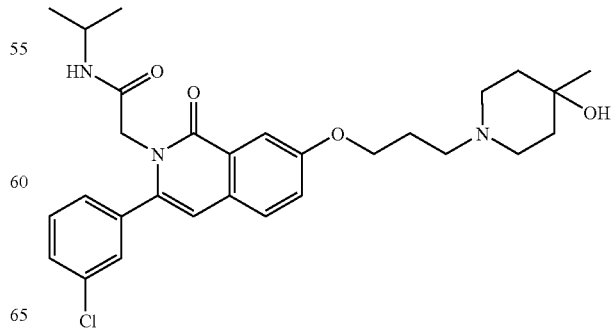

MS (ESI) m/z: 526/528 ([M+H]+) (from INTERMEDIATE III.7 & 4-hydroxy-4-methylpiperidine)

Example 32

N-tert-Butyl-2-{3-(3-Chlorophenyl)-7-[3-(4-hydroxy-4-methyl-piperidin-1-yl)-propoxy]-1-oxo-1H-isoquinolin-2-yl}acetamide

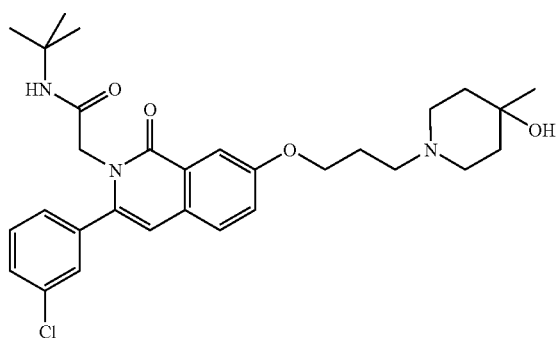

MS (ESI) m/z: 540/542 ([M+H]+) (from INTERMEDIATE III.8 & 4-hydroxy-4-methylpiperidine)

Example 33

2-[7-[3-(4-Hydroxy-4-methylpiperidin-1-yl)-propoxy]-3-(3-methoxyphenyl)-1-oxo-1H-isoquinolin-2-yl]-N-isopropylacetamide

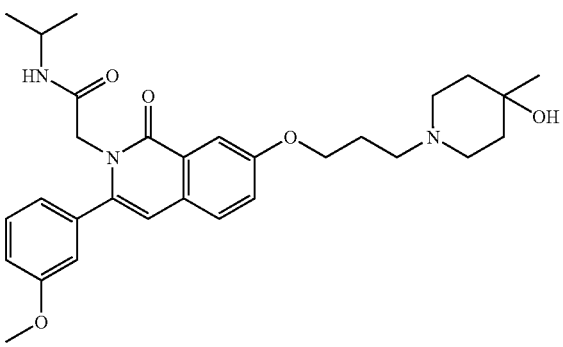

MS (ESI) m/z: 522 ([M+H]+ (from INTERMEDIATE III.3 & 4-hydroxy-4-methylpiperidine)

Example 34

N-tert-Butyl-2-[7-[3-(4-hydroxy-4-methylpiperidin-1-yl)propoxy]-3-(3-methoxyphenyl)-1-oxo-1H-isoquinolin-2-yl]acetamide

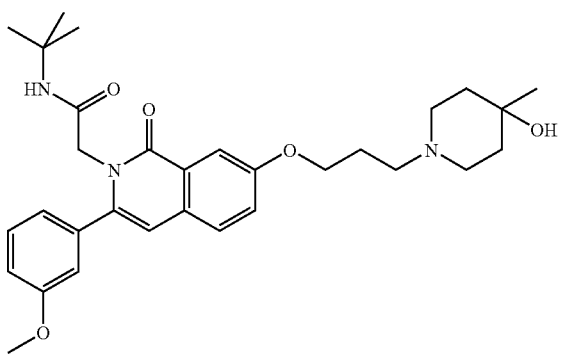

MS (ESI) m/z: 522 ([M+H]+) (from INTERMEDIATE III.4 & 4-hydroxy-4-methylpiperidine)

Example 35

2-[3-(3-Chlorophenyl)-1-oxo-7-(3-piperidin-1-ylmethylphenyl)-1H-isoquinolin-2-yl]-N-isopropylacetamide

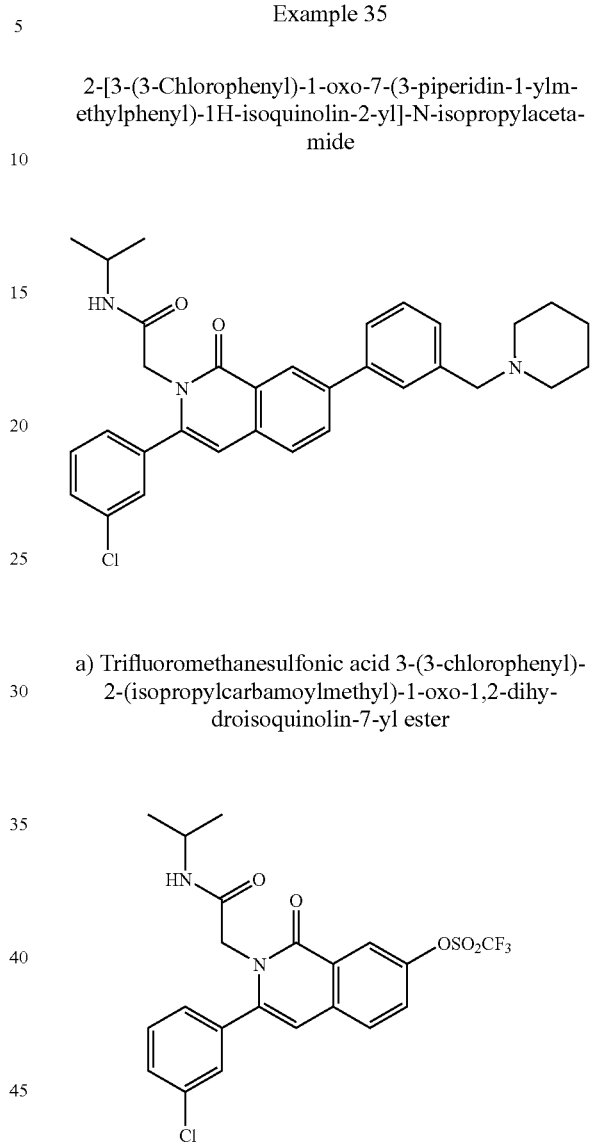

a) Trifluoromethanesulfonic acid 3-(3-chlorophenyl)-2-(isopropylcarbamoylmethyl)-1-oxo-1,2-dihydroisoquinolin-7-yl ester To 2-[3-(3-chlorophenyl)-7-hydroxy-1-oxo-1H-isoquinolin-2-yl]-N-isopropylacetamide (INTERMEDIATE III.7) (0.60 g, 1.6 mmol) in dry pyridine (15 mL) at 0° C. was added trifluoromethanesulfonic anhydride (0.27 mL, 1.6 mmol) dropwise. After the addition the ice bath was removed and the reaction mixture was stirred for 2 h at room temperature. The mixture was then concentrated in vacuo and the crude residue taken up in EtOAc and washed with 1 N HCl (aq.) (1×20 mL) and brine (1×20 mL). The organic phase was dried (MgSO$_4$), filtered and concentrated in vacuo to afford trifluoromethanesulfonic acid 3-(3-chlorophenyl)-2-(isopropylcarbamoylmethyl)-1-oxo-1,2-dihydroisoquinolin-7-yl ester (0.66 g, 1.3 mmol, 82%) as an orange solid, which was used without further purification. Data for trifluoromethanesulfonic acid 3-(3-chlorophenyl)-2-(isopropylcarbamoylmethyl)-1-oxo-1,2-dihydroisoquinolin-7-yl ester: MS (ESI), m/z: 444/446 ([M–C$_3$H$_8$N]+).

b) 2-[3-(3-Chlorophenyl)-7-(3-hydroxymethylphenyl)-1-oxo-1H-isoquinolin-2-yl]-N-isopropylacetamide

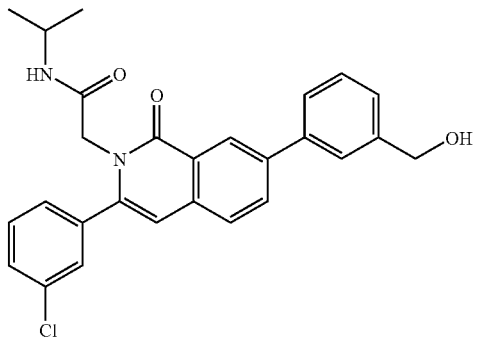

To a solution of trifluoromethanesulfonic acid 3-(3-chlorophenyl)-2-(isopropylcarbamoylmethyl)-1-oxo-1,2-dihydroisoquinolin-7-yl ester (0.10 g, 0.20 mmol) in acetone (2 mL) and water (1 mL) was added 3-hydroxymethylphenyl boronic acid (0.10 g, 0.65 mmol), $K_2CO_3$ (100 mg, 0.72 mmol) and $(Ph_3P)_4Pd$ (20 mg, 0.017 mmol). The vessel was sealed and heated at 60° C. for 1 hour. The mixture was cooled to 0° C. and 2-[3-(3-chlorophenyl)-7-(3-hydroxymethylphenyl)-1-oxo-1H-isoquinolin-2-yl]-N-isopropylacetamide was collected by filtration and used in the next step without further purification.

Data for 2-[3-(3-chlorophenyl)-7-(3-hydroxymethylphenyl)-1-oxo-1H-isoquinolin-2-yl]-N-isopropylacetamide: MS (ESI) m/z: 461/463 ([M+H]$^+$).

c) 2-[7-(3-Chloromethylphenyl)-3-(3-chlorophenyl)-1-oxo-1H-isoquinolin-2-yl]-N-isopropylacetamide

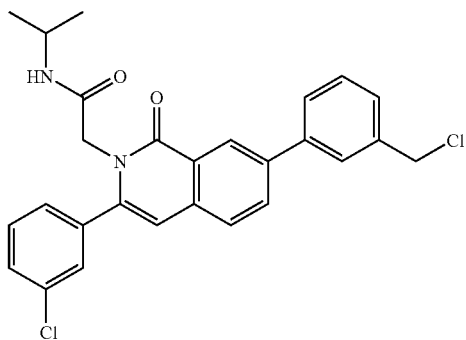

To a solution of crude 2-[3-(3-chlorophenyl)-7-(3-hydroxymethylphenyl)-1-oxo-1H-isoquinolin-2-yl]-N-isopropylacetamide (100 mg, 0.22 mmol) in DCM (5 mL) was added $SOCl_2$ (0.5 mL, 6.8 mmol) and the reaction mixture was stirred at 23° C. for 2 h. The solution was concentrated in vacuo and the crude residue purified by chromatography on silica gel with MeOH:DCM (1:19, v/v) as eluent to yield 2-[7-(3-chloromethylphenyl)-3-(3-chlorophenyl)-1-oxo-1H-isoquinolin-2-yl]-N-isopropylacetamide (19 mg, 0.40 mmol, 20% for 2 steps from trifluoromethanesulfonic acid 3-(3-chlorophenyl)-2-(isopropylcarbamoylmethyl)-1-oxo-1,2-dihydroisoquinolin-7-yl ester as yellow solid.

d) 2-[3-(3-Chlorophenyl)-1-oxo-7-(3-piperidin-1-ylmethylphenyl)-1H-isoquinolin-2-yl]-N-isopropylacetamide (EXAMPLE 35)

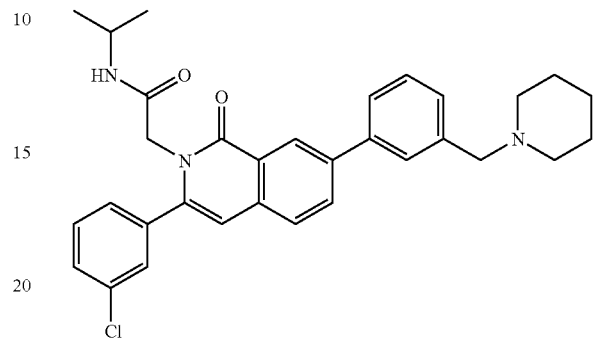

To 2-[7-(3-chloromethylphenyl)-3-(3-chlorophenyl)-1-oxo-1H-isoquinolin-2-yl]-N-isopropylacetamide (19 mg, 0.04 mmol) in DCM (5 mL) was added piperidine (0.5 mL) and this was stirred at 23° C. for 18 h. The mixture was concentrated in vacuo, and the crude residue purified by preparative HPLC to yield the HCl salt of 2-[3-(3-chlorophenyl)-1-oxo-7-(3-piperidin-1-ylmethylphenyl)-1H-isoquinolin-2-yl]-N-isopropylacetamide (EXAMPLE 35) hydrochloride salt (7 mg, 0.013 mmol, 33%) as pale beige solid.

Data for 2-[3-(3-chlorophenyl)-1-oxo-7-(3-piperidin-1-ylmethylphenyl)-1H-isoquinolin-2-yl]-N-isopropylacetamide (EXAMPLE 35) hydrochloride salt: $^1$H NMR (300 MHz, CD$_3$OD) δ 8.64 (d, 1H), 8.2-7.4 (m, 11H), 6.71 (s, 1H), 4.59 (s, 2H), 4.42 (s, 2 H), 3.95 (septet, 1 H), 3.54 (br d, 2H), 3.05 (br t, 2H) 2.0-1.5 (m, 6H), 1.11 (d, 6H) ppm; MS (ESI) m/z: 528/530 ([M+H]$^+$)

EXAMPLE 36 was prepared in a similar manner:

Example 36

N-tert-Butyl-2-[3-(3-methoxyphenyl)-1-oxo-7-(3-piperidin-1-ylmethylphenyl)-1H-isoquinolin-2-yl] acetamide

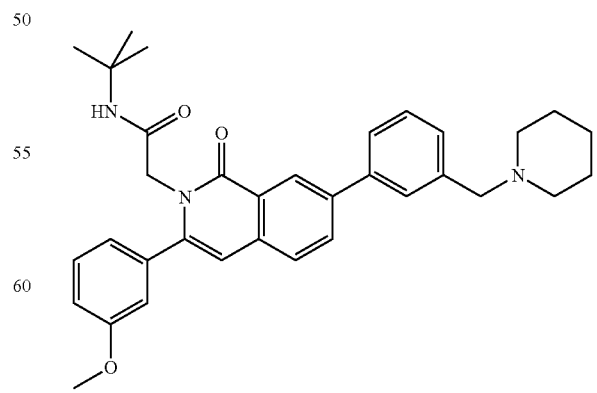

MS (ESI) m/z: 538 ([M+H]$^+$) (from INTERMEDIATE III.4 & piperidine)

Example 37

Chinese Hamster Ovary (CHO) cells stably expressing the human $V_3$ receptor were incubated to equilibrium with the test compound (at a final assay concentration of $10^{-10}$ mol.$L^{-1}$ to $10^{-5}$ mol.$L^{-1}$) and [$^3$H]AVP (at a final assay concentration of $2.5\times10^{-9}$ mol.$L^{-1}$). Throughout the concentration of dimethylsulphoxide (DMSO) did not exceed 0.1% (v/v). After washing with ice-cold phosphate buffered saline (PBS), scintillation fluid was added and the plates counted on a Topcount NXT apparatus.

A sigmoidal dose response curve (non-linear regression, variable slope) was plotted as concentration of test compound (mol.$L^{-1}$) against percentage specific binding of [$^3$H]AVP and a $K_i$ value was calculated. Each determination was carried out in triplicate and repeated on at least 3 separate occasions Table 1 shows the binding activity obtained for some representative compounds of the invention.

TABLE 1

$V_3$ binding activity for compounds according to the invention

| | | |
|---|---|---|
| EXAMPLE 3: 2-[7-((S)-3-Dimethylamino-2-methylpropoxy)-3-(3-fluorophenyl)-1-oxo-1H-isoquinolin-2-yl]-N-isopropylacetamide | 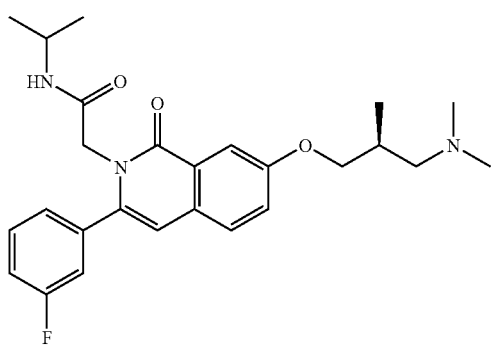 | ++ |
| EXAMPLE 14: N-Isopropyl-2-[3-(3-methoxyphenyl)-7-((S)-2-methyl-3-piperidin-1-ylpropoxy)-1-oxo-1H-isoquinolin-2-yl]acetamide | 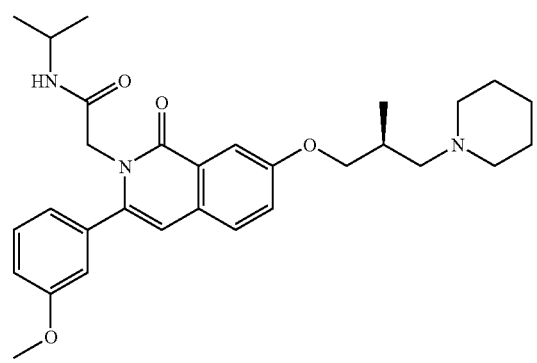 | + |
| EXAMPLE 23: N-tert-Butyl-2-[3-(6-methoxypyridin-2-yl)-1-oxo-7-(3-pyrrolidin-1-ylpropoxy)-1H-isoquinolin-2-yl]acetamide | 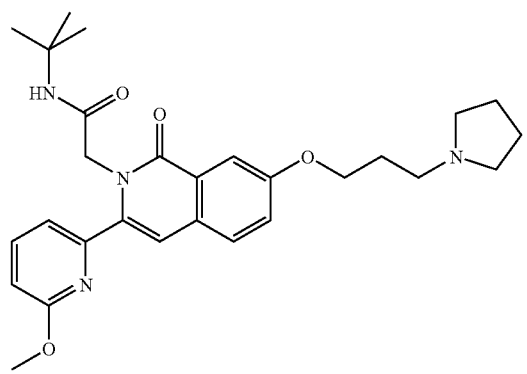 | ++ |

TABLE 1-continued

V$_3$ binding activity for compounds according to the invention

EXAMPLE 26: N-Isopropyl-2-[1-oxo-3-phenyl-7-(3-piperidin-1-ylpropoxy)-1H-isoquinolin-2-yl]acetamide

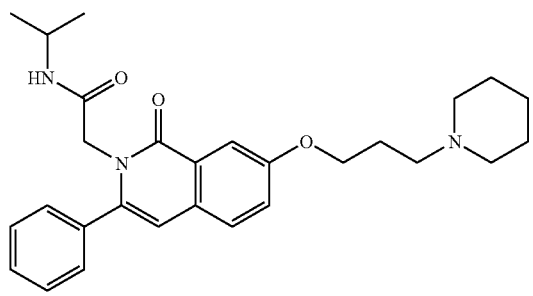

+++

EXAMPLE 28: N-tert-Butyl-2-[3-(3-chloro-4-fluorophenyl)-1-oxo-7-(3-pyrrolidin-1-ylpropoxy)-1H-isoquinolin-2-yl]acetamide

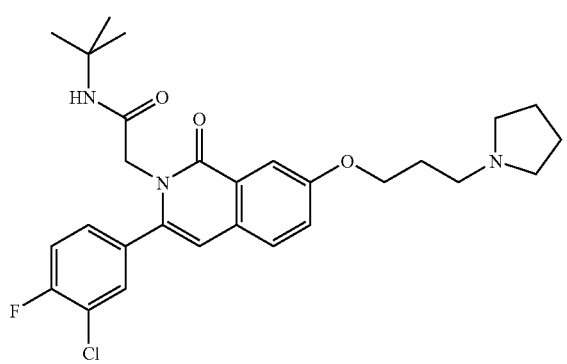

+

EXAMPLE 35: 2-[3-(3-Chlorophenyl)-1-oxo-7-(3-piperidin-1-ylmethylphenyl)-1H-isoquinolin-2-yl]-N-isopropylacetamide

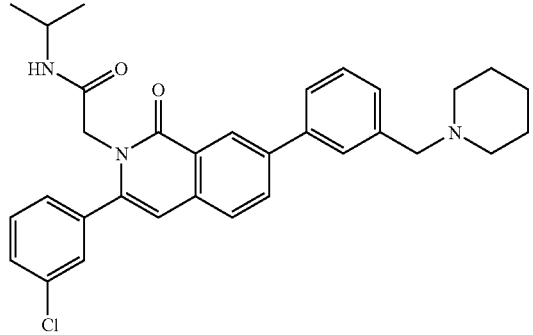

++

+++ 0-10 nM
++ 10-100 nM
+ 100 nM-1 uM

The ability of compounds of the invention to act as V$_3$ antagonists in a physiologically relevant system was determined by measuring their ability to block the release of adrenocorticotropic hormone (ACTH) from anterior pituitary corticotrophs in response to treatment with arginine vasopressin (AVP).

Anterior pituitary corticotrophs were prepared from adult female Sprague-Dawley rats and seeded into 48 well plates. The cells were cultured for 4 days prior to exposure to compound. Test compounds were prepared at $10^{-5}$ mol.L$^{-1}$ in 100% DMSO. Cells were exposed to a dose response of test compounds for 20 minutes ($10^{-8}$ mol.L$^{-1}$–$10^{-5}$ mol.L$^{-1}$). The final concentration of DMSO in the assay was kept constant at 0.3%. The cells were then exposed to $3\times10^{-9}$ mol.L$^{-1}$ AVP for 120 minutes. Supernatants were harvested and stored at −20° C. ACTH levels were subsequently measured by ELISA following the manufacturer's instructions (Immunodiagnostic systems, UK (Cat No. DX-SDX018)). Each treatment was carried out in quadruplicate and a mean value obtained for the amount of ACTH released. The degree of antagonism was then calculated as a percentage of the amount of ACTH released by agonist alone after adjustment for basal levels of ACTH. A pIC$_{50}$ was calculated by fitting a Sigmoidal dose response (variable slope) curve with a non-linear (fit) to the data using the software package GraphPad prism. Each determination was repeated on at least 3 separate occasions Table 2 shows the activity obtained for some representative compounds of the invention.

TABLE 2

V₃ receptor antagonism in isolated rat anterior pituitary cells for compounds according to the invention

| | | |
|---|---|---|
| EXAMPLE 1: 2-[3-(3-Chlorophenyl)-7-((S)-2-methyl-3-pyrrolidin-1-ylpropoxy)-1-oxo-1H-isoquinolin-2-yl]-N-isopropylacetamide | 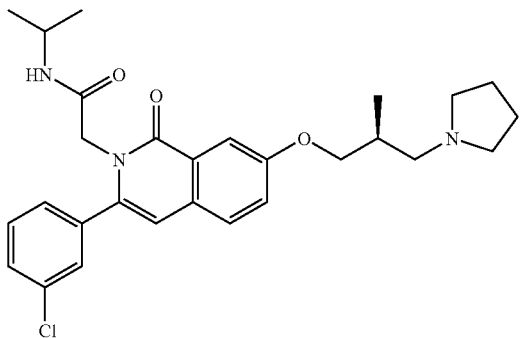 | + |
| EXAMPLE 17: N-tert-Butyl-2-{3-(3-chlorophenyl)-7-[3-(4-hydroxypiperidin-1-yl)-propoxy]-1-oxo-1H-isoquinolin-2-yl}-acetamide | 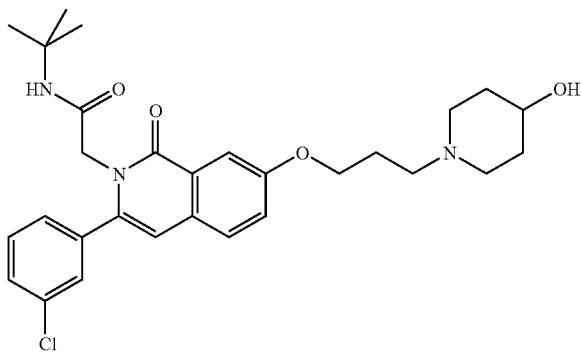 | ++ |

++ 10-100 nM
+ 100 nM-1 uM

The invention claimed is:

1. A 2-(1-oxo-1H-isoquinolin-2-yl)acetamide compound of formula I,

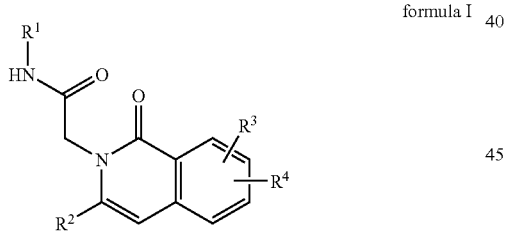

formula I wherein $R^1$ is $C_{1-6}$alkyl, $C_{3-6}$cycloalkyl, $C_{3-6}$cycloalkyl$C_{1-2}$alkyl, $C_{2-6}$alkenyl or $C_{2-6}$alkynyl, said $C_{1-6}$alkyl, $C_{3-6}$cycloalkyl and $C_{3-6}$cycloalkyl$C_{1-2}$alkyl being optionally substituted with one or more halogens;

$R^2$ is $C_{6-10}$aryl optionally substituted with one to three substituents selected from halogen, hydroxy, cyano, $C_{1-6}$alkyl, $C_{3-6}$cycloalkyl, $C_{1-6}$alkyloxy and $C_{3-6}$cycloalkyloxy, said $C_{1-6}$alkyl, $C_{3-6}$ cycloalkyl, $C_{1-6}$ alkyloxy and $C_{3-6}$cycloalkyloxy being optionally substituted with one or more halogens or $R^2$ is a 5-10 membered heteroaryl ring system comprising a heteroatom selected from N, O, S and optionally substituted with a substituent selected from methyl, $C_{1-6}$alkyloxy and halogen;

$R^3$ is an optional substituent selected from $C_{1-6}$alkyl, $C_{1-6}$alkyloxy and halogen, said $C_{1-6}$alkyl and $C_{1-6}$alkyloxy being optionally substituted with one or more halogens;

$R^4$ is a group located at the 6- or 7-position of the oxoisoquinoline ring and is selected from

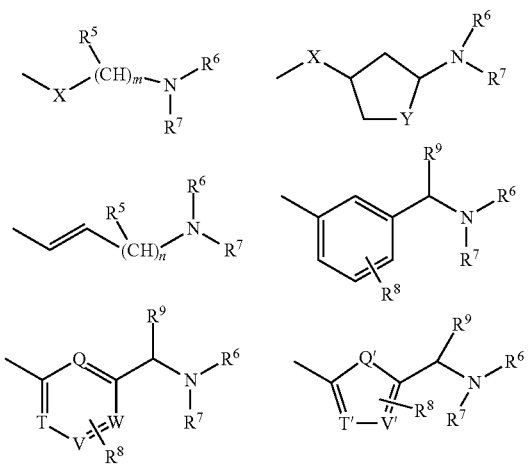

each $R^5$ is independently H or $C_{1-6}$alkyl or one of $R^5$ when joined together with one of $R^6$ or $R^7$ forms a 4-7 membered heterocyclic ring;

$R^6$ and $R^7$ are independently H, $C_{1-6}$alkyl, $C_{3-6}$cycloalkyl, $C_{3-6}$cycloalkyl$C_{1-2}$alkyl, $C_{6-10}$ aryl or $C_{6-10}$aryl$C_{1-2}$alkyl; or $R^6$ and $R^7$ together with the nitrogen to which they are bonded form a 4 to 8 membered saturated or unsaturated heterocyclic ring optionally comprising a further heteroatomic moiety selected from O, S and $NR^{10}$, said heterocyclic ring being optionally substituted with one or two substituents selected from halogen, hydroxyl, $C_{1-6}$alkyl, $C_{1-6}$alkyloxy, cyano and $COOR^{11}$ and said heterocyclic ring being optionally fused at two adjacent carbon atoms to a phenyl ring;

or one of $R^6$ and $R^7$ when joined together with one of $R^5$ forms a 4-7 membered heterocyclic ring;

or one of $R^6$ and $R^7$ when joined together with one of $R^8$ forms a 5-6 membered heterocyclic ring;

$R^8$ is one or two substituents selected from H, $C_{1-6}$alkyl, $C_{1-6}$alkyloxy and halogen or one of $R^8$ when joined together with one of $R^6$ and $R^7$ forms a 5-6 membered heterocyclic ring;

or one of $R^8$ when joined together with $R^9$ forms a 5-6 membered ring $R^9$ is H or $C_{1-6}$alkyl or $R^9$ when joined together with one of $R^8$ forms a 5-6 membered ring;

$R^{10}$ is H, $C_{1-6}$alkyl or $C_{1-6}$acyl;

$R^{11}$ is H or $C_{1-6}$alkyl;

m is 2-4;

n is 1-3;

X is $CH_2$, O, S, $SO_2$ or $NR^{12}$;

$R^{12}$ is H, $C_{1-6}$alkyl, $C_{1-6}$acyl or $C_{6-10}$aryl$C_{1-2}$alkyl group, said $C_{6-10}$-aryl$C_{1-2}$alkyl group being optionally substituted with methyl or methoxy;

Y is $CH_2$, $(CH_2)_2$ or $(CH_2)_3$;

Q, T, V and W are C or N with the proviso that one of Q, T, V and W is N and the others are C;

Q', T' and V' are selected from C, O, N and S with the proviso that one of Q', T' and V' is O, N, or S and the others are C;

or a pharmaceutically acceptable salt thereof.

2. The 2-(1-oxo-1H-isoquinolin-2-yl)acetamide compound according to claim 1, wherein $R^1$ is isopropyl, isobutyl, tertiary-butyl or cyclopropylmethyl.

3. The 2-(1-oxo-1H-isoquinolin-2-yl)acetamide compound according to claim 1, wherein $R^2$ is a substituted phenyl ring selected from 3-chlorophenyl, 3-fluorophenyl, 3-methoxyphenyl, 3-trifluoromethoxyphenyl, 3-chloro-4-fluorophenyl and 4-fluoro-3-methoxyphenyl.

4. The 2-(1-oxo-1H-isoquinolin-2-yl)acetamide compound according to claim 1, wherein $R^4$ is a substituent at the 7-position of the oxoisoquinoline ring.

5. The 2-(1-oxo-1H-isoquinolin-2-yl)acetamide compound according to claim 1, wherein $R^4$ is a group selected from

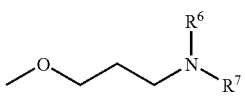
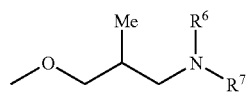

-continued

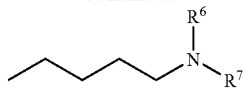

wherein $R^6$ and $R^7$ have the previously defined meanings.

6. The 2-(1-oxo-1H-isoquinolin-2-yl)acetamide compound according to claim 1, wherein $R^4$ is a group selected from

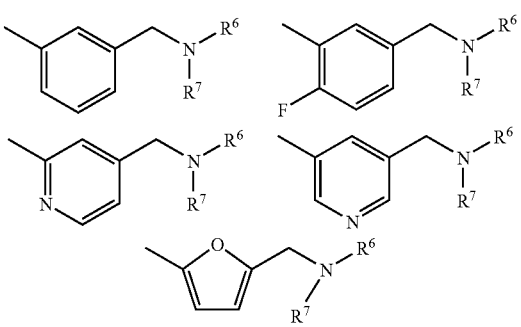

wherein $R^6$ and $R^7$ have the previously defined meanings.

7. The 2-(1-oxo-1H-isoquinolin-2-yl)acetamide compound according to claim 1, wherein $R^6$ and $R^7$ are independently H or $C_{1-4}$-alkyl.

8. The 2-(1-oxo-1H-isoquinolin-2-yl)acetamide compound according to claim 1, wherein $R^6$ and $R^7$ together with the nitrogen to which they are bonded form a heterocyclic ring selected from pyrrolidine, piperidine, 3-hydroxypiperidine and morpholine.

9. A 2-(1-oxo-1H-isoquinolin-2-yl)acetamide compound selected from:

N-tert-Butyl-2-[3-(4-fluoro-3-methoxyphenyl)-1-oxo-7-(3-pyrrolidin-1-ylpropoxy)-1H-isoquinolin-2-yl]acetamide;

2-[3-(3-Chlorophenyl)-7-((S)-2-methyl-3-pyrrolidin-1-ylpropoxy)-1-oxo-1H-isoquinolin-2-yl]-N-isopropylacetamide and N-tert-Butyl-2-[3-(3-chloro-4-fluorophenyl)-1-oxo-7-(3-pyrrolidin-1-ylpropoxy)-1H-isoquinolin-2-yl]acetamide or a pharmaceutically acceptable salt thereof.

10. A pharmaceutical composition comprising a 2-(1-oxo-1H-isoquinolin-2-yl)acetamide compound according to claim 1, or a pharmaceutically acceptable salt thereof, in admixture with one or more pharmaceutically acceptable auxiliaries.

11. A pharmaceutical composition comprising a 2-(1-oxo-1H-isoquinolin-2-yl)acetamide compound according to claim 9, or a pharmaceutically acceptable salt thereof, in admixture with one or more pharmaceutically acceptable auxiliaries.

* * * * *

UNITED STATES PATENT AND TRADEMARK OFFICE
CERTIFICATE OF CORRECTION

| | | |
|---|---|---|
| PATENT NO. | : 7,906,504 B2 | Page 1 of 1 |
| APPLICATION NO. | : 11/852737 | |
| DATED | : March 15, 2011 | |
| INVENTOR(S) | : Letourneau et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 0 days.

Signed and Sealed this
Fifth Day of July, 2011

David J. Kappos
*Director of the United States Patent and Trademark Office*